US012746214B2

(12) United States Patent
Liu et al.

(10) Patent No.: US 12,746,214 B2
(45) **Date of Patent: *Sep. 29, 2026**

(54) COLOR-CHANGING ANTIBACTERIAL NANOFIBER

(71) Applicant: UNIVERSITY OF MANITOBA, Winnipeg (CA)

(72) Inventors: Song Liu, Winnipeg (CA); Sarvesh Logsetty, Winnipeg (CA)

(73) Assignee: University of Manitoba, Winnipeg (CA)

( * ) Notice: Subject to any disclaimer, the term of this patent is extended or adjusted under 35 U.S.C. 154(b) by 1138 days.

This patent is subject to a terminal disclaimer.

(21) Appl. No.: 17/487,285

(22) Filed: Sep. 28, 2021

(65) Prior Publication Data

US 2022/0047523 A1 Feb. 17, 2022

Related U.S. Application Data

(63) Continuation-in-part of application No. 17/227,940, filed on Apr. 12, 2021, now Pat. No. 11,911,521, which is a continuation of application No. 16/138,577, filed on Sep. 21, 2018, now Pat. No. 10,973,775.

(60) Provisional application No. 63/086,631, filed on Oct. 2, 2020, provisional application No. 62/561,943, filed on Sep. 22, 2017.

(51) Int. Cl.

| | |
|---|---|
| ***A61K 9/70*** | (2006.01) |
| ***A61F 13/00*** | (2024.01) |
| ***A61F 13/01*** | (2024.01) |
| ***A61K 9/00*** | (2006.01) |
| ***A61K 47/32*** | (2006.01) |
| ***A61K 47/34*** | (2017.01) |
| ***A61L 15/24*** | (2006.01) |
| ***A61L 15/26*** | (2006.01) |
| ***A61L 15/46*** | (2006.01) |
| ***A61P 17/02*** | (2006.01) |
| ***A61P 31/04*** | (2006.01) |
| ***B82Y 30/00*** | (2011.01) |
| ***D01D 5/00*** | (2006.01) |
| ***D01F 1/10*** | (2006.01) |
| ***D01F 8/10*** | (2006.01) |
| ***D01F 8/14*** | (2006.01) |

(52) U.S. Cl.

CPC ...... *A61K 9/7007* (2013.01); *A61F 13/01017* (2024.01); *A61K 9/0092* (2013.01); *A61K 9/703* (2013.01); *A61K 47/32* (2013.01); *A61K 47/34* (2013.01); *A61L 15/24* (2013.01); *A61L 15/26* (2013.01); *A61L 15/46* (2013.01); *A61P 17/02* (2018.01); *A61P 31/04* (2018.01); *D01D 5/0007* (2013.01); *D01F 1/103* (2013.01); *D01F 8/10* (2013.01); *D01F 8/14* (2013.01); *A61F 2013/00089* (2013.01); *A61L 2300/208* (2013.01); *A61L 2300/404* (2013.01); *A61L 2300/604* (2013.01); *A61L 2400/12* (2013.01); *B82Y 30/00* (2013.01)

(58) Field of Classification Search

None

See application file for complete search history.

(56) References Cited

U.S. PATENT DOCUMENTS

| | | | | |
|---|---|---|---|---|
| 4,382,953 | A | 5/1983 | Ishii et al. | |
| 10,973,775 | B2 | 4/2021 | Liu et al. | |
| 11,911,521 | B2 * | 2/2024 | Liu | A61K 9/7007 |
| 2001/0006644 | A1 * | 7/2001 | Bova | A61K 31/465 424/400 |
| 2002/0177139 | A1 | 11/2002 | Greenfield et al. | |
| 2006/0057183 | A1 | 3/2006 | Nakano et al. | |
| 2007/0265243 | A1 | 11/2007 | Turos et al. | |
| 2010/0291182 | A1 | 11/2010 | Palasis et al. | |
| 2015/0258195 | A1 | 9/2015 | Almutairi et al. | |
| 2019/0091167 | A1 | 3/2019 | Liu et al. | |

FOREIGN PATENT DOCUMENTS

| | | | | |
|---|---|---|---|---|
| WO | WO-2014027707 A1 * | 2/2014 | | A61F 13/0206 |

OTHER PUBLICATIONS

Currie et al. ACS Appl. Mater. Interfaces 2020, 12, 45859-45872. (Year: 2020).*

Pillay et al. Journal of Nanomaterials, vol. 2013, pp. 1-22; publication year: 2013. (Year: 2013).*

English Machine Translation of Kim WO2014/027707 [online]. Google Patents [retrieved on Apr. 11, 2025]. Retrieved from the internet <https://patents.google.com/patent/WO2014027707A1/en?oq=WO2014%2f027707>. (Year: 2025).*

Miyaji et al., Letters in Applied Microbiology; vol. 42, pp. 242-247 (Year: 2006).

Shah et al., Annals of Microbiology vol. 58, No. 3, pp. 381-386 (Year: 2008).

Augustine et al., Electrospun PCL membranes incorporated with biosynthesized silver nanoparticles as antibacterial wound dressings, Appl Nanosci (2016) 6:337-344, DOI 10.1007/s13204-015-0439-1.

Bean et al., Triggered release of Bacteriophage K from agarose/hyaluronan hydrogel matrixes by *Staphylococcus aureus* virulence factors, Chem. Mater. 26 (2014) 7201-7208. doi: 10.1021/cm503974g.

(Continued)

*Primary Examiner* — Katherine Peebles

(74) *Attorney, Agent, or Firm* — CALDERON SAFRAN & WRIGHT P.C.

(57) ABSTRACT

A bacteria-responsive color-changing, core-shell nanofiber, comprising polyurethane (PU), a hemicyanine-based chromogenic probe localized in the core-shell nanofiber near the surface of the shell, polyvinylpyrrolidone (PVP) dopant in the shell, the hemicyanine-based chromogenic probe further comprising a labile ester linkage that is enzymatically cleavable by bacterial lipase released from clinically relevant strains of bacteria including *Pseudomonas aeruginosa* and methicillin-resistant *Staphylococcus aureus* (MRSA).

7 Claims, 19 Drawing Sheets
(5 of 19 Drawing Sheet(s) Filed in Color)

(56) References Cited

OTHER PUBLICATIONS

Bessa et al., Bacterial Isolates from Infected Wounds and Their Antibiotic Susceptibility Pattern: Some Remarks about Wound Infection. Int. Wound J. (2015), 12 (1), 47-52.
Boardman et al., The Prevention of In-Wash Dye Transfer. Rev. Prog. Color. Relat. Top. (2000), 30 (1), 63-66.
Borodko et al., Charge-Transfer Interaction of Poly(Vinylpyrrolidone) with Platinum and Rhodium Nanoparticles. J. Phys. Chem. C (2007), 111 (17), 6288-6295.
Cai et al., Using Polyvinylpyrrolidone to Enhance the Enzymatic Hydrolysis of Lignocelluloses by Reducing the Cellulase Non-Productive Adsorption on Lignin. Bioresour. Technol. (2017), 227, 74-81.
Cefalu et al., Wound Infections in Critical Care. Crit. Care, Nurs. Clin. North Am. (2017), 29, 81-96.
Craig et al., Bacterial protease triggered release of biocides from microspheres with an oily core, Colloids Surfaces B Biointerfaces. 127 (2015) 200-205. doi:10.1016/j.colsurfb.2015.01.036.
De Queiroz et al., Resistive-Type Humidity Sensors Based on PVP-Co and PVP-I2 Complexes. J. Polym. Sci. Part B Polym. Phys. (2001), 39, 459-469 (Abstract).
Dessouki et al., Gamma Ray Induced Graft Copolymerization of N-Vinylpyrrolidone, Acrylamide and Their Mixtures onto Polypropylene Films. Polym. Int. (1998), 45 (1), 67-76.
Edwards et al., Bacteria and Wound Healing. Curr. Opin. Infect. Dis. (2004), 17, 91-96.
Gardner et al., The Validity of the Clinical Signs and Symptoms Used to Identify Localized Chronic Wound Infection. Wound Repair Regen. (2001), 9 (3), 178-186.
He et al., Fabrication of metronidazole loaded poly (e-caprolactone)/zein core/shell nanofiber membranes via coaxial electrospinning for guided tissue regeneration, J. Colloid Interface Sci. 490 (2017) 270-278. doi:10.1016/j.cis.2016.11.062.
Hoang et al., Degradation of polyethylene succinate (PES) by a new thermophilic Microbispora strain, Biodegradation. 18 (2007) 333-342. doi:10.1007/s10532-006-9067-5.
Li et al., Diagnostics for Wound Infections. Adv. Wound Care (2020), 1-36. https://doi.org/10.1089/wound.2019.1103.
Lin et al., Zwitterionized Chitosan Based Soft Membranes for Diabetic Wound Healing. J. Memb. Sci. (2019), 591, 117319.
Liu et al., A PH-Indicating Colorimetric Tough Hydrogel Patch towards Applications in a Substrate for Smart Wound Dressings. Polymers (Basel). (2017), 9 (558), 1-15.
Liu et al., Electrospun PLGA/Collagen Nanofibrous Membrane as Early-Stage Wound Dressing. J. Memb. Sci. (2010), 355, 53-59.
Martin et al., Molecular Microbiology: New Dimensions for Cutaneous Biology and Wound Healing. J. Invest. Dermatol. (2010), 130, 38-48.
Pallapolu et al., Boost Effect of Water- Soluble Polymers on Enzymatic Hydrolysis of Lignocellulosic Biomass. Ind. Eng. Chem. Res. (2020), 59, 5186-5193 (Abstract).
Ross et al., Comparison of the Efficacy of Silver-Based Antimicrobial Burn Dressings in a Porcine Model of Burn Wounds. Burns (2020). https://doi.org/10.1016/j.burns.2020.04.004.
Ruostesuo et al., Charge Transfer Complexes of N-Substituted 2-Pyrrolidinones. Spectrochim. Acta (1988), 44A (1), 63-67.
Singh et al., Lipase-Responsive Electrospun Theranostic Wound Dressing for Simultaneous Recognition and Treatment of Wound Infection. ACS Appl. Bio Mater. (2019), 2 (5), 2028-2036.
Spindler et al., Physical and Spectroscopic Properties of Ternary Polymer Electrolytes Composed of Poly 'Vinylpyrrolidone), Poly(Ethylene Glycol), and Lithium Trifluoromethanesulfonate. Macromolecules (1986), 19 (2), 347-350.
Sun et al., Colorimetric Band-Aids for Point-of-Care Sensing and Treating Bacterial Infection. ACS Cent. Sci. (2020), 6 (2), 207-212. (11).
Teng et al., A TCF-Based Colorimetric and Fluorescent Probe for Palladium Detection in an Aqueous Solution. Tetrahedron Lett. (2018), 59 (29), 2804-2808.
Thet et al., Prototype Development of the Intelligent Hydrogel Wound Dressing and Its Efficacy in the Detection of Model Pathogenic Wound Biofilms, ACS Appl. Mater. Interfaces. 8 (2016) 14909-14919. doi:10.1021/acsami.5b07372.
Traba & Liang, Bacteria responsive antibacterial surfaces for indwelling device infections, J. Control. Release. 198 (2015) 18-25. doi:10.1016/j.jconrel.2014.11.025.
Tsiouris et al., Human Microflora, Probiotics and Wound Healing. Wound Med. (2017), 19, 33-38.
Venault et al., Zwitterionic Electrospun PVDF Fibrous Membranes with a Well-Controlled Hydration for Diabetic Wound Recovery. J. Memb. Sci. (2020), 598, 117648.
Xiong et al., Lipase-sensitive polymeric triple-layered nanogel for "on-demand" drug delivery, J. Am. Chem. Soc. 134 (2012a) 4355-4362. doi:10.1021/ja211279u.
Xiong et al., Bacteria-Responsive Multifunctional Nanogel for Targeted Antibiotic Delivery, Advanced Materials, 24 (46) December (2012) 6175-6180. doi: 10.1002/adma.201202847.
Yang et al., Promotion of skin regeneration in diabetic rats by electrospun core-sheath fibers loaded with basic fibroblast growth factor, Biomaterials. 32 (2011) 4243-4254. doi:10.1016/j.biomaterials.2011.02.042.
Yapor et al., Polydiacetylene Nanofiber Composites as a Colorimetric Sensor Responding to *Escherichia coli* and Ph. Acs Omega (2017), 2 (10), 7334-7342.
Yu et al., Large Scale Production of Hexagonal ZnO Nanoparticles Using PVP as a Surfactant. Mater. Lett. (2016), 166, 284-287.
Zhou et al., Bacteria-Responsive Intelligent Wound Dressing: Simultaneous In Situ Detection and Inhibition of Bacterial Infection for Accelerated Wound Healing. Biomaterials (2018), 161, 11-23.
European Wound Management Association (EWMA). Position Document: Identifying Criteria for Wound Infection; London: MEP Ltd, (2006).
Bowler et al., Wound Microbiology and Associated Approaches to Wound Management. Clin. Microbiol. Rev. (2001), 14 (2), 244-269.
Majewski et al., The Value of Quantitative Bacteriological Investigations in the Monitoring of Treatment of Ischaemic Ulcerations of Lower Legs. Int. Angiol. (1995), 14, 381-384 (Abstract).
Raahave et al., The Infective Dose of Aerobic and Anaerobic Bacteria in Postoperative Wound Sepsis. Arch. Surg. 1986, 121, 924-929 (Abstract).
Voronova et al., Preparation and Characterization of Polyvinylpyrrolidone/Cellulose Nanocrystals Composites. Nanomaterials (2018), 8 (12), 1-21.

* cited by examiner

| Sample code | Sample name | Bacteria concentration CFU/cm² | Exposure time | Degree of Hydrolysis (%) |
|---|---|---|---|---|
| S-H-15 Min | Single PU | $10^{10}$ | 15 Minutes | 57 |
| CS-H-15 Min | Core-shell PU | $10^{10}$ | 15 Minutes | 58 |
| PVP-H-15 Min | Core-shell PU:PVP | $10^{10}$ | 15 Minutes | 92 |
| S-L-3 Hr | Single PU | $10^{5}$ | 3 Hours | 0 |
| CS-L-3 Hr | Core-shell PU | $10^{5}$ | 3 Hours | 35 |
| PVP-L-3 Hr | Core-shell PU:PVP | $10^{5}$ | 3 Hours | 42 |

A B

C

D

| Dye | Exact Mass | Detected Mass | | Yellow intensity % | Red intensity % |
|---|---|---|---|---|---|
| | | Yellow | Red | | |
| Yellow | 401.1017 | 400.1565 | 302.0830 | 100% | 4.1% |
| Red | 303.100 | - | 302.0820 | - | 100% |
| Green | 401.1017<br>303.100 | 400.1539 | 302.0816 | 100% | 19% |

| Reflected color | Absorbed color | E (eV): Excitation Energy |
| --- | --- | --- |
| Yellow | Violet | 2.25 |
| Red | Green | 1.5 |
| Green | Red | 0.75 |

$\Delta E_1 > \Delta E_2 > \Delta E_3$

Absorbed Energy= ΔE

COLOR-CHANGING ANTIBACTERIAL NANOFIBER

CROSS REFERENCE TO RELATED APPLICATIONS

This application is a continuation-in-part and claims benefit of U.S. patent application Ser. No. 17/227,940 filed Apr. 12, 2021 by the University of Manitoba (Applicant), entitled "ANTIBACTERIAL NANOFIBER" which is a continuation and claims the benefit of U.S. patent application Ser. No. 16/138,577 filed Sep. 21, 2018 and now U.S. Pat. No. 10,973,775. The disclosures of U.S. patent application Ser. No. 16/138,577 are incorporated herein by reference in their entirety. This application claims the benefit of U.S. provisional patent application No. 63/086,631 filed Oct. 2, 2020 entitled "Highly sensitive bacteria-responsive membranes consisting of core-shell polyurethane polyvinylpyrrolidone electrospun nanofibers for in situ detection of bacterial infections" assigned to the University of Manitoba as Applicant and named inventors Song Liu and Sarvesh Logsetty, and which is expressly incorporated herein by reference in its entirety and to which priority is claimed. This application claims the benefit of U.S. provisional patent application No. 62/561,943 filed Sep. 22, 2017 entitled "Antibacterial Nanofiber" assigned to the University of Manitoba as Applicant and named inventors Song Liu and Sarvesh Logsetty, and which is expressly incorporated herein by reference in its entirety and to which priority is claimed.

The patent or application file contains a least one drawing executed in color. Copies of this patent or patent application publication with color drawing(s) will be provided by the Office upon request and payment of the necessary fee.

FIELD OF THE INVENTION

The present disclosure relates generally to antibacterial materials for use in wound healing.

BACKGROUND OF THE INVENTION

Wound infection is a global healthcare issue that affects the healing process. Appropriate wound dressing material can reduce the risk of infection by reducing or eliminating the invasion of pathogens. The use of antibacterial materials or agents in wound dressings can reduce risk of infection.

One approach to wound healing involves exposure of the wound to antibacterial drug release using systems that continuously elute an antibacterial agent, even if there is no bacterium present. This unnecessary release of an antibacterial agent is poorly timed with the need for the agent, and may cause undesirable cytotoxicity to the subject. Such cytotoxicity may impart delays in the healing process. Systems involving a constant and indiscriminant elution may result in a depletion of the antibacterial agent before exposure to bacteria occurs, and consequently may be ineffective when needed.

It desirable to provide materials for use in wound healing that provide antibacterial properties when needed in the presence of bacteria. All wounds contain some level of bacterial contamination that might not delay wound healing. However, after bacterial load has progressed to a critical level, wound infection ensues which leads to an inflammatory response and potential tissue damage in the host. Early detection and treatment of rising bacterial load in a wound can aid healing.

Typically, a bacterial load of $10^5$ colony forming units (CFU) per gram of tissue is considered the critical threshold for wound infection. Beyond this threshold, symptoms arising from host immune response to bacterial infection such as inflammation, pain, purulent discharge, swelling and tissue damage may cause patient discomfort and impede wound healing. Clinical assessment requires progression of infection to a symptomatic level; however, it is more desirable to diagnose and treat infections before the infection develops. Conventional methods such as tissue biopsy, curettage and wound swabbing, each have major shortcomings related to painful and invasive procedures, and the delay in treatment due to the time required for sample analysis.

For example, a wound swab may identify some or all of the bacteria within the wound, but significant waiting is required for the accurate identification of wound infection. Also, swabbing a wound entails removal of the dressing, which is associated with pain and secondary trauma to the wound bed. In addition to the laboratory techniques (swabbing and culturing), imaging techniques such as magnetic resonance imaging (MRI), ultrasound imaging, and plain radiography (X-ray) also have applications in infection detection (8). However, the same as laboratory techniques, imaging techniques require wound dressing removal. The need for frequent dressing changes results in secondary trauma to the wound bed, added pain and cost to patient care. The shortcomings of the common techniques for infection detection necessitate a non-invasive, non-disturbing, inexpensive and reliable method for early detection of infection. In situ detection through smart wound dressing is an alternative to surmount the mentioned issues and reduce human intervention and errors.

Intelligent wound dressings for diagnostic management of bacterial infections offer a platform for continuous monitoring of wound bed health with the goal of enabling early detection of bacteria at the critical threshold prior to the establishment of infection. Several dressings for in situ detection of bacteria have been developed in recent years. For example, Zhou et al. developed a gelatin-based membrane containing fluorescent vesicles lysable by bacterial toxins from methicillin-resistant *Staphylococcus aureus* (MRSA) or *Pseudomonas aeruginosa*. Sun et al. have demonstrated pH-sensitive paper-based dressings capable of selectively sensing drug-responsive and drug-resistant *Escherichia coli*. Thet et al. have produced agarose films that display fluorescence after contact with biofilms of clinically relevant bacteria such as *S. aureus* and *P. aeruginosa*, and Liu et al. have demonstrated pH-responsive alginate hydrogel patches. However, the current methods are limited by the sensitivity and response time of the membranes, as well as the nature of the chromogenic response, since it is desirable to have a color change visible with the naked eye to promote easy diagnosis of bacterial presence by healthcare providers. Furthermore, there is a lack of correlation between the clinically used units for bacterial concentration (CFU/cm2) and the sensitivity of diagnostic dressings in previously published work, which implement units such as CFU/mL or fail to quantify the limit of detection of the dressing.

Electrospun nanofibers provide an ideal substrate for improving the sensitivity and response time of diagnostic wound dressings due to their high specific surface area. Additionally, electrospun membranes are well-suited as wound dressings in general since their nanoporous structure mimics that of the natural extracellular matrix, and also contributes to appropriate gas exchange rate and exudate absorption. In a previous study, (Singh, H.; Li, W.; Kazemian, M. R.; Yang, R.; Yang, C.; Logsetty, S.; Liu, S.

Lipase-Responsive Electrospun Theranostic Wound Dressing for Simultaneous Recognition and Treatment of Wound Infection. *ACS Appl. Bio Mater.* 2019, 2 (5), 2028-2036.) the results of which are incorporated herein by reference, a chromogenic probe was synthesized with an ester linkage that can be hydrolyzed by bacterial lipase to facilitate a color change from yellow to red in the presence of lipase producing bacteria. Blended into an electrospun nanofibrous polyurethane (PU) membrane, the dye showed a response after 4 h incubation with a high concentration of *P. aeruginosa* (˜108 CFU/mL).

SUMMARY OF THE INVENTION

It is an object of the present invention to obviate or mitigate at least one disadvantage of previous antibacterial materials or wound healing materials.

It is also an objective to enable early detection of wound infection and enable intervention to prevent tissue damage and delayed wound healing.

There is provided a core-shell nanofiber comprising: a core comprising an antibacterial agent and a biocompatible polymer; and a shell surrounding the core comprising a bacterially degradable polymer.

Further, there is provided a core-shell nanofiber comprising: a core comprising benzyl dimethyl tetradecyl ammonium chloride (BTAC) and poly(vinylpyrrolidone) (PVP); and a shell comprising polycaprolactone (PCL) and poly (ethylene succinate) (PES).

A process is described for the preparation of an antibacterial core-shell nanofiber comprising: coaxially electrospinning a fiber from a core material within a shell material to thereby form the antibacterial core-shell nanofiber; wherein: the core material comprises an antibacterial agent and a biocompatible polymer; and the shell material comprises a bacterially degradable polymer.

Further, a nanofiber mat and a wound dressing are described comprising the nanofiber.

Additionally, a process is described for fabricating a core-shell fiber highly sensitive to the presence of bacterial lipase.

In a broad aspect, the present invention comprises a bacteria-responsive color-changing nanofibers, including any feature described, either individually or in combination with any feature, in any configuration.

In another broad aspect, the present invention provides a method to construct a bacteria-responsive color-changing nanofibers comprising any process described, in any order, using any modality, either individually or in combination with any feature, in any configuration.

In another broad aspect, the present invention provides a bacteria-responsive color-changing, core-shell nanofiber comprising polyurethane (PU) and a hemicyanine-based chromogenic probe with a labile ester linkage that is enzymatically cleavable by bacterial lipase released from clinically relevant strains of bacteria.

In another aspect, the present invention provides a bacteria-responsive color-changing, core-shell nanofiber that includes polyvinylpyrrolidone (PVP) dopant in the shell, and a hemicyanine-based chromogenic probe localized in the core-shell nanofiber near the surface of the shell to achieve rapid chromogenic response.

In another aspect, the present invention detects bacteria strains including at least one of *Pseudomonas aeruginosa* and methicillin-resistant *Staphylococcus aureus* (MRSA).

In another broad aspect, the present invention provides a bacteria-responsive color-changing nanofiberous membrane, comprising polyurethane (PU) core-shell nanofibers and a hemicyanine-based chromogenic probe with a labile ester linkage that is enzymatically cleavable by bacterial lipase released from clinically relevant strains of bacteria.

In another aspect, the present invention provides a bacteria-responsive color-changing nanofiberous membrane that includes polyvinylpyrrolidone (PVP) dopant in the shell of core-shell nanofibers, and the probe is localized in the core-shell nanofibers near the surface of the shell to achieve rapid chromogenic response.

In another broad aspect, the present invention provides a process to construct a highly sensitive electrospun nanofibrous membrane, the process comprising electrospinning polyurethane to produce core-shell fiber and incorporating in said polyurethane a hemicyanine-based chromogenic probe with a labile ester linkage that can be enzymatically cleaved by bacterial lipase released from clinically relevant strains.

In another aspect, the present invention provides a process that includes localizing a chromogenic probe at the surface of said core-shell fibers to effect rapid chromogenic response, and incorporating polyvinylpyrrolidone (PVP) dopant in the shell to boost sensitivity.

In another aspect, the present invention provides a process further comprising including polyvinylpyrrolidone (PVP) in the shell of a core-shell fiber in an electrospun membrane to boost the degree of hydrolysis of the chromogenic probe.

Other aspects and features of the present disclosure will become apparent to those ordinarily skilled in the art upon review of the following description of specific embodiments in conjunction with the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present disclosure will now be described, by way of example only, with reference to the attached Figures.

DETAILED DESCRIPTION OF THE PREFERRED EMBODIMENT(S)

Figure 1:
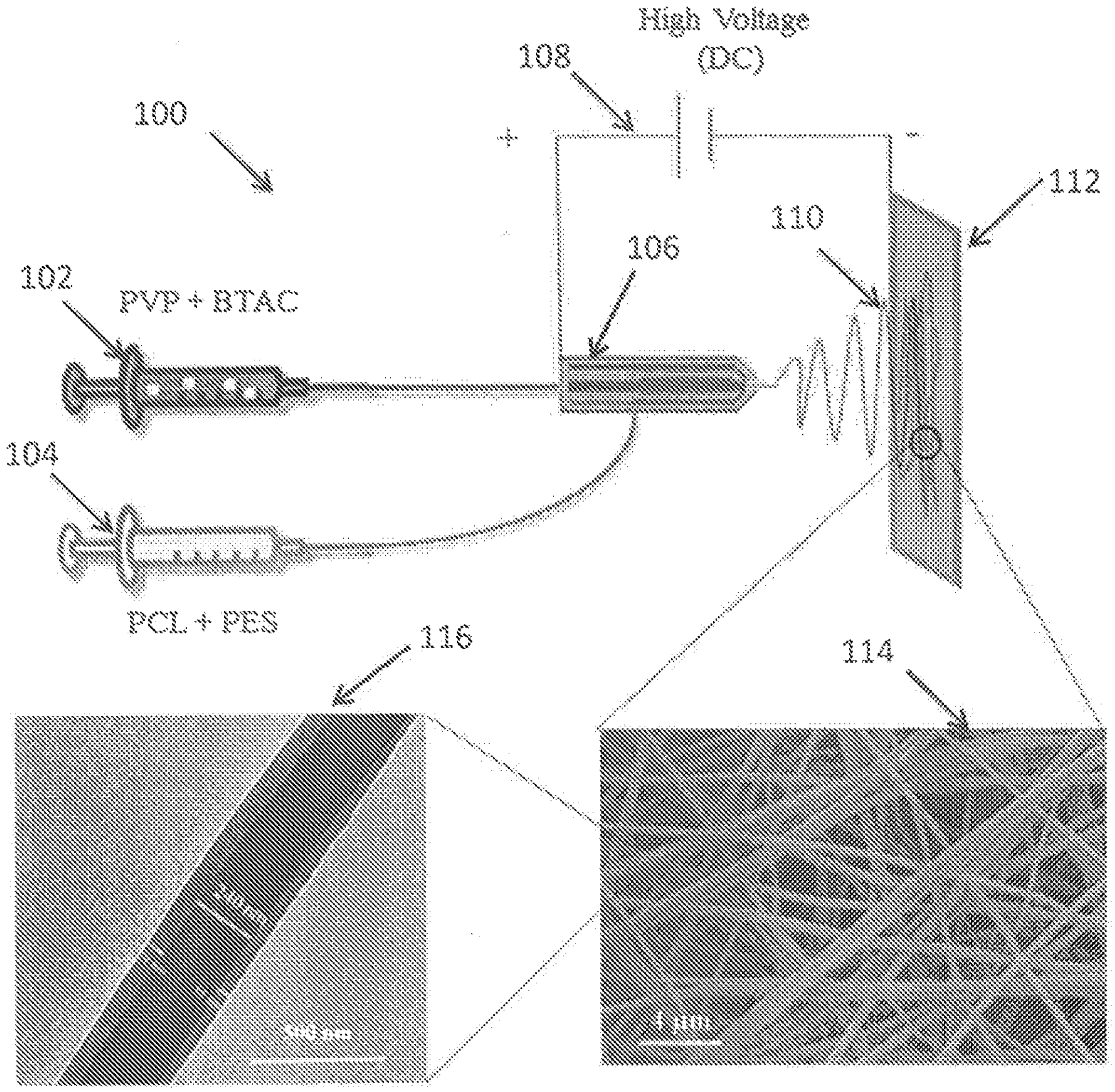
FIG. 1 is a schematic representation of the process for fabrication of nanofibers.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Generally, the present disclosure provides an antibacterial nanofiber that changes color and releases an antibacterial agent in response to the presence of bacteria.

Tackling bacterial infection without compromising wound healing can be addressed by using the antibacterial nanofibers described herein. The nanofibers may, for example, be used in preparation of bacteria responsive wound dressings.

The antibacterial nanofiber comprises a core formed of a biocompatible polymer and an antibacterial agent. The core has a very fine width, and is coated with a bacteria degradable polymer. The biocompatible polymer of the core may be a water soluble polymer.

A core-shell nanofiber is described herein. The nanofiber comprises a core comprising an antibacterial agent and a biocompatible polymer; and a shell surrounding the core comprising a bacterially degradable polymer.

The antibacterial agent may be any acceptable agent, such as a drug or biocide. For example, the agent may comprise a quaternary ammonium compound (QAC). An exemplary antibacterial agent is benzyl dimethyl tetradecyl ammonium chloride (BTAC).

The biocompatible polymer of the core may comprise any polymer that would support the antibacterial agent, and remain biocompatible, such as poly(vinylpyrrolidone) (PVP). An exemplary core may comprise BTAC and PVP.

The shell is formulated so that the bacterially degradable polymer is degraded by bacterial activity in its proximity, such as bacterial enzyme activity or by a drop in pH to 6 or less, indicative of bacterial activity. An exemplary bacterial enzyme is lipase. The polymer from which the shell is formulated is advantageously degradable by lipase. For example, the shell may comprise polycaprolactone (PCL) or poly(ethylene succinate) (PES), or both.

An exemplary core-shell nanofiber is described which comprises: a core comprising benzyl dimethyl tetradecyl ammonium chloride (BTAC) and poly(vinylpyrrolidone) (PVP); and a shell comprising polycaprolactone (PCL) and poly(ethylene succinate) (PES).

The core may consist substantially of only BTAC and PVP; and the shell may consist essentially of PCL and PES, but other components may be added to the core and the shell.

When present in the core, BTAC may be present in an amount of from about 1% to about 10%, by weight of the core, such as from 2% to 5%.

When present, the ratio of PCL to PES may be from about 1:5 to about 5:1, such as 1:1.

The ratio of the core to the shell may be from about 1:5 to about 5:1 by weight, such as from 1:2 to 2:1 by weight.

A process is provided herein for preparation of an antibacterial core-shell nanofiber. The process comprises coaxially electrospinning a fiber from a core material within a shell material to thereby form the antibacterial core-shell nanofiber; wherein: the core material comprises an antibacterial agent and a biocompatible polymer; and the shell material comprises a bacterially degradable polymer.

Optionally, the electrospinning may comprise application of a voltage from about 5 kV to about 50 kV, such as 20 kV.

Core-shell nanofibers prepared by the above process are described herein.

A nanofiber mat comprising a plurality of core-shell nanofibers is described.

An antibacterial wound dressing comprising the core-shell or the nanofiber mat may be used, as described herein.

Further, a method is described for treating a wound, the method comprising applying to the wound the antibacterial wound described herein.

An single electrospun antibacterial nanofiber is also described herein, which comprises polycaprolactone (PCL), poly(ethylene succinate) (PES), and from about 2 to 5% (by weight) BTAC as an antibacterial agent. The single electrospun fiber possesses antibacterial activity.

Single spinning may be used to fabricate bacteria responsive wound dressing for combatting bacterial infection, and for on-demand release of an antibacterial agent.

When bacteria is present in a wound, bacterial activities such as lipase secretion and release of products that act to cause an acidic pH, are able to degrade the shell polymer, exposing the core. Once the shell becomes adequately degraded, the antibacterial agent is released from the core in the location where it is needed, at a time when bacteria is present.

Wound dressings formed of or incorporating such antibacterial fibers are encompassed herein, such as may be made from other materials and impregnated or coated with the nanofibers or nanofiber mats described herein.

As referred to herein, an "antibacterial agent" encompasses a drug, a biocide, or an antimicrobial compound, which may include compounds or combinations of compounds having anti-fungal, anti-bacterial or anti-viral activity. The antibacterial agent is incorporated in the nanofiber, protected from exposure to bacteria although remaining in an active form. The agent is thus exposed, so as to assert its antibacterial properties, only on an as-needed basis.

The nanofibers described herein are bacteria responsive systems that are degraded in response to bacteria, and provide on-demand antibacterial agent release, such as drug or biocide release. More controllable release of core-shell nanofibers permits a controllable release, while single nanofibers provide efficient and prolonged bacteria killing activity. The selective release of antibacterial agents by these nanofibers and efficacy against bacteria was accompanied by high viability of mammalian cells tested. Thus, efficient antibacterial activity of nanofibers without comprising wound healing makes these nanofibers advantageous for use in wound dressings to avoid or alleviate wound infections, and in other applications where antibacterial activity is required.

The present invention provides a bacteria responsive color-changing wound dressings that enable continuous monitoring of the wound bed facilitating early detection of bacterial infection. The present invention provides a highly sensitive electrospun nanofibrous polyurethane wound dressing, incorporating a hemicyanine-based chromogenic probe with a labile ester linkage that can be enzymatically cleaved by bacterial lipase released from clinically relevant strains such as *Pseudomonas aeruginosa* and methicillin-resistant *Staphylococcus aureus* (MRSA). A rapid chromogenic response can be achieved by localizing the dye at the surface of core-shell fibers, resulting in a 5× faster response relative to conventional nanofibers. By incorporating polyvinylpyrrolidone (PVP) dopant in the shell, the sensitivity can be boosted to enable detection of bacteria at clinically relevant concentrations after 2 h exposure: 2.5×$10^5$ CFU/$cm^2$ *P. aeruginosa* and 1.0×$10^6$ CFU/$cm^2$ MRSA. Introduction of PVP in the shell also boosts the degree of hydrolysis of the chromogenic probe by a factor of 1.2× after 3 h exposure to a low concentration of *P. aeruginosa* ($10^5$ CFU/$cm^2$). Development tests for the present invention that PVP also improves the discernibility of the color change at high bacterial concentrations. The co-operativity between the chromogenic probe, fiber structure and polymer composition of the present invention is well-suited for timely in situ detection of wound infections.

In the present invention, HCy dye is localized in the shell of core-shell PU nanofibers to enable a faster rate of color changing response, with approximately 5× faster color changing response relative to single-electrospun fibers. PVP dopant in the shell of the core-shell PU nanofibers can be incorporated in two ratios (CS-PU:PVP 4:1 and CS-PU:PVP 2:1) to improve the sensitivity of the fibers, achieving a color change observable by the naked eye after 2 h exposure to 2.5×$10^5$ CFU/$cm^2$ *P. aeruginosa* and 1.0×$10^6$ CFU/$cm^2$ MRSA, which approaches the critical threshold of bacteria in the wound bed prior to the development of delayed wound healing and symptomatic infection. The PVP dopant also produces a more dark and vivid green color change at high bacteria concentrations, improving ease of detection. The boosted rate of detection and vividness of color change achieved by incorporating PVP into the fibers are attributable to several factors including intermolecular charge transfer between PVP and HCy due to donor/acceptor interaction with PVP in aqueous solution, reduced wash-out of the dye due to formation of HCy-PVP complex, and action of PVP as a surfactant to expose HCy to improve the degree of hydrolysis of HCy. The incorporation of PVP and core-shell structure boosts the degree of hydrolysis by a factor of 1.2× and enhances the change in hue of the membranes in CIE L*C*h color space by 22-fold. Ultimately, the relationship between core-shell structure, polymer composition and membrane function can be exploited for the creation of highly sensitive wound dressings capable of detecting critical bacteria concentrations to diagnose wound infection in the early stages.

The present invention incorporates a synthesized hemicyanine-based dye with an ester linkage that can be hydrolyzed by bacterial lipase, resulting in increased intramolecular charge transfer (ICT) between the phenolate ion and hemicyanine group accompanied by a characteristic absorbance shift from 424 nm to 575 nm with a visual color change from yellow to red.

Bacteria-Responsive Nanofibers for On-demand Release of Antibacterial Agents to Address Wound Infections Nanofibers have been used as biocompatible materials for wound healing in recent years. In this example, core-shell nanofibers are prepared and used to provide triggered release of an antibacterial agent. Due to bacterial activity, such as lipase secretion and acidification of pH, degradation of the shell material was facilitated and resulted in the release of an incorporated antibacterial agent present in the core of the nanofiber. Bacteria triggered release of an antibacterial agent can advantageously replace other antibacterial strategies that deploy unneeded release of antibacterial agents and which may result in cytotoxicity to a subject. The nanoscopic and core-shell structure of the nanofibers were finely confirmed by scanning electron microscopy (SEM) and transmission electron microscopy (TEM). Due to bacterial activity, nanofibers were degraded in bacterial supernatant at significantly higher levels than in non-enzymatic solutions. Moreover, bacteria responsive core-shell nanofibers showed a more controllable release of the antibacterial agent, which resulted in prolonged effective antibacterial efficacy, and lower cytotoxicity to fibroblast cells.

Skin injuries especially chronic wounds are a global healthcare issue and the healing process of a wound is highly influenced by the wound dressing material. The use of antibacterial agents to eliminate invasion and colonization of pathogens in a wound is an important aspect in the wound dressing. Antibacterial agents have been incorporated into different biomaterials for antibacterial activity (Augustine et al, 2016). Previous approaches to the design of antibacterial releasing systems have involved continuous release of bioactive compounds, even if no bacteria is present. This unneeded release of antibacterial agents could cause undesirable cytotoxicity, which can delay the healing process. Further, continuous elution may deplete the system of its antibacterial agent before infection occurs. This would render such systems ineffective, and poses additional pressure on healthcare costs. Treatment failure and prolonged therapy may be the result of such systems (Craig et al., 2016). Therefore, it is important to address infection without compromising wound healing.

To reduce the misuse and overuse of antibacterial agents, a bacteria-responsive system may be used. Bacteria possess different virulence factors, which can act as triggers for such systems (see, for example Thet et al., 2016; and Traba & Liang 2015). As a result, a system would release its antimicrobial payload only when interacting with bacteria. Enzymes are a virulence factor that may be used to trigger a bacteria responsive systems. For example, hyaluronidase enzymes secreted by *S. aureus* have been used for triggering release of bacteriophage K embedded in a photo-cross-linkable hyaluronic acid based hydrogel (Bean et al., 2014). In *S. aureus*, the protease enzyme was used to stimulate degradation of polypeptide based drug-loaded particles (Craig et al., 2015).

Unlike hyaluronidase enzyme which is mostly secreted by Gram-positive bacteria with little to no excretion in gram negative bacteria, lipase is secreted by both Gram-positive and Gram-negative bacteria. As compared to protease enzyme that naturally presents in extracellular matrix (ECM) and is secreted by white blood cells in the wound site, lipase is mostly the product of bacteria.

Lipase-labile bonds, such as fatty acid esters or anhydrides can be degraded in response to lipase. Polycaprolactone (PCL) is a biodegradable polyester with the low hydrolytic degradation. A lipase sensitive triple-layered nanogel (TLN) has been used as a carrier for on-demand drug delivery (Xiong et al., 2012a). In this approach, the TLN contained a PCL interlayer between the cross-linked polyphosphoester core and the shell of poly(ethylene glycol). The PCL fence of TLN was subjected to degradation by the activity of bacterial lipases.

A rapid rate of response is desirable. The faster a system responds to a triggering factor secreted by bacteria, the more effective the system will be. The rate of response is dependent on both physical and chemical structure of the system. Systems with a large surface area such as nanoparticles and nanofibers, may be triggered faster.

In the system described in this example is an electrospun polymeric nanofiber having high porosity and excellent pore interconnectivity. This system leads to advantages for use in wound dressing materials. The nanofiber described permits intimate contact with wound areas despite highly variable or irregular wound shapes and sizes. Thus, the protection of an open wound from external physical pressures and contamination would be facilitated using the described nanofiber. Further, a greater opportunity for the self-healing process to occur, and lower risk of scar formation is provided by the described nanofiber. Permeability of the nanofiber, and of wound dressings made from the nanofiber, to moisture and air allows the extraction of wound exudate to provide a moisturized environment and prevent infection.

Polycaprolactone (PCL) has the advantage of being a biodegradable synthetic polymer, with excellent biocompatibility and efficacy both in vitro and in vivo. However, its highly hydrophobic nature and slow degradation has previously hindered its use in biomedical applications, such as in wound dressings. To overcome this limitation, PCL can be blended with another biodegradable polymer. Poly(ethylene succinate) (PES) is an aliphatic biodegradable polyester, which has higher rate of degradation than PCL (Hoang et al., 2007).

In this example, electrospun nanofibrous mats are prepared based on PCL and PES, with effective degradation in response to bacteria.

Single electrospun nanofibers are prepared, which due to the superficial effect in a nanoscale size, the antibacterial agent (drug) particles in the single electrospun nanofibers tend to accumulate on the surface of the fibers prepared. Therefore, a large amount of the antibacterial agent is released at the initial stage of bacterial infection in an uncontrolled manner. As a consequence, whenever an infection lasts for a prolonged time, much of the antimicrobial content of wound dressing may have been released in early stage of infection. These main drawbacks in the use of antimicrobial wound dressings can be avoided through the use of core-shell nanofibers fabricated through co-axial electrospinning (He et al., 2017; Yang et al., 2011).

In this example, two immiscible solutions are pushed through two concentrically located needles that form a single outlet. As the solutions are pumped out of the needles, the outer polymer (or "shell") material covers the inner (or "core") material, which comprises an antimicrobial agent or drug. As a result, the polymer nanofibers so formed have a core-shell structure. Drug preservation in the core material prevents the uncontrolled release of the drug, and ensures even distribution of the drug, which leads to prolonged antimicrobial efficacy.

The core-shell nanofibers prepared have a PCL/PES shell, and contain as a drug within the core: benzyl dimethyl tetradecyl ammonium chloride (BTAC) for antibacterial activity. In the core material, the BTAC is dissolved in poly(vinylpyrrolidone) (PVP), which serves as core. The nanofibers form nanofiber mats, which have the potential to be degraded in response to bacteria. Drug release and antibacterial efficacy of single and core-shell nanofibers are compared. Morphology, diameter, and the core-sell structure of nanofibers are evaluated using SEM and TEM. Cytotoxicity of the nanofibers was evaluated.

Materials and Methods

The described nanofiber comprises a shell of polycaprolactone and poly(ethylene succinate); and a core of poly (vinylpyrrolidone) as the core polymer and benzyl dimethyl tetradecyl ammonium chloride (BTAC) as the core antibacterial agent. Bacterial activity, comprising lipase secretion and acidic pH, was used to degrade the shell. Once the shell became adequately degraded, the antibacterial agent was released from the core. Further details are outlined below.

Materials

Polycaprolactone (PCL) 80,000 MW, poly(ethylene succinate) (PES) 10,000 MW, poly(vinylpyrrolidone) (PVP) 40,000 MW, dimethylformamide (DMF), dichloromethane (DCM), benzyl dimethyl tetradecyl ammonium chloride (BTAC) as an antibacterial drug, 3-(4,5-Dimethyl-2-thiazolyl)-2,5-diphenyl-2H-tetrazolium bromide (MTT), dimethyl sulfoxide (DMSO), and orange II sodium salt were purchased from Sigma.

The structure of the polymers are as shown below.

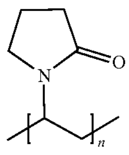

Poly (vinylpyrrolidone) (PVP)

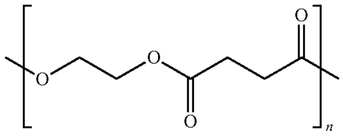

Poly(ethylene succinate) (PES)

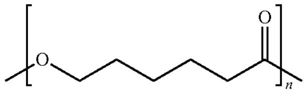

Polycaprolactone (PCL)

An Inoveso electrospining apparatus (Model Ne300, Turkey), was used to fabricate single and core-shell nanofibers. *Staphylococcus aureus* (*S. aureus*-ATCC 29213) and *Escherichia coli* (*E-coli*-ATCC 25922) were used as gram positive and gram negative bacteria. ATCC-PCS-201 neonatal human dermal fibroblast was purchased from Cedarlane Corporation, Canada.

Fabrication of Nanofibers

PCL and PES were dissolved in DCM:DMF (4:1) at a concentration of 8 wt % uncontrolled manner and 20 wt %. PCL solution (8 wt %) was mixed with PES solution (20 wt %) in volume ratios of (PCL:PES) 5:1, 2:1, and 1:1. Then, the mixed solutions were subjected to the single electrospinning experiment. Voltage (20 kV), flow rate of solution (1 mL/h), and distance between syringe and collector (18 cm) were set for each of the samples.

For core-shell electrospinning, PVP was considered as core component and the same solution in the single nanofibers as shell component. PVP was dissolved in DCM:DMF (4:1) at a concentration of 15 wt %. Flow rates of core and shell solution were 0.3 and 1 ml/h, respectively.

To prepare drug loaded nanofibers, BTAC was dissolved in DCM and added to PCL/PES blend for single nanofibers or to PVP for core-shell nanofibers. 2.5%, 3.5%, and 4.5% of BTAC with respect to weight of whole polymer was used to study the antibacterial efficacy of nanofibers. The sample codes are listed in Table 1.

TABLE 1

Feed composition of fabricated nanofibers

| Sample code | Feed composition |
|---|---|
| PCL:PES 5:1 | PCL 8% + PES 20% |
| PCL:PES 2:1 | |
| PCL:PES 1:1 | |
| S 2.5 | Single electrospining: |
| S 3.5 | PCL 8% + PES 30% (1:1) + 2.5, 3.5, and 4.5% BTAC |
| S 4.5 | |
| CS 2.5 | Co-axial electrospining: |
| CS 3.5 | Shell: PCL 8% + PES 30% (1:1) |
| CS 4.5 | Core: PVP 15% + 2.5, 3.5, and 4.5% BTAC |

FIG. 1 shows a schematic representation of the process (100) for fabrication of nanofibers. Briefly, a blend of PVP and BTAC is provided in a core syringe (102), while a blend of PCL and PES is provided in the shell syringe (104), which are combined in a common extruding syringe (106), subjected to a voltage (108) of 20 kV, and the nanofiber (110) was collected at a collector (112). A photomicrograph of the nanofiber mat (114) formed and of an individual fiber (116) are shown.

Figure 2:
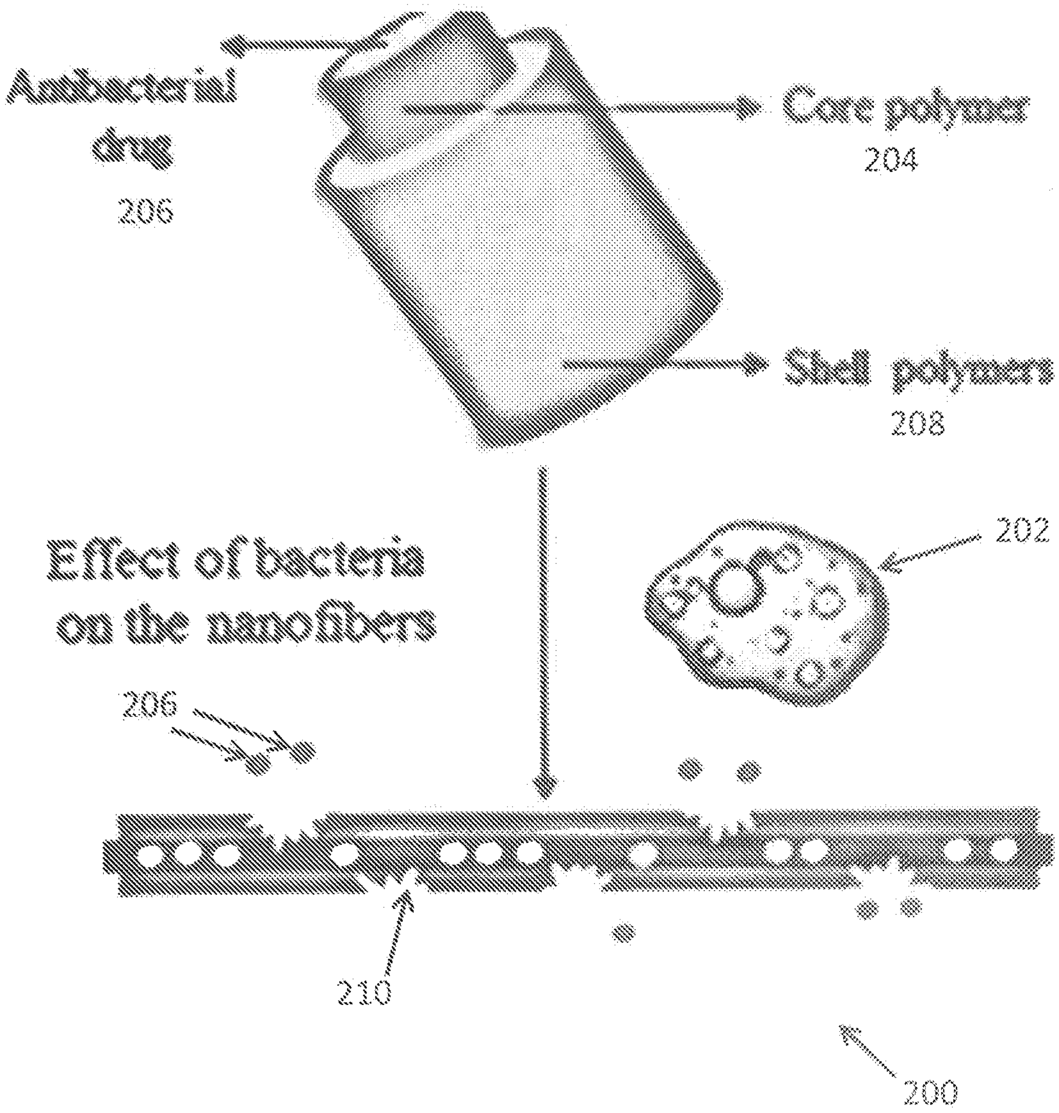
FIG. 2 is an illustration of a core-shell nanofiber, and an overview of the degradation process by bacteria.

FIG. 2 provides a diagrammatic illustration of the resulting nanofiber, and an overview of the degradation process (200) by bacteria (202). The nanofiber comprises the core polymer (204) which contains an antibacterial drug (206), and the shell polymer (208). Upon exposure to the bacteria (202) a degraded fiber (210) is formed, from which the antibacterial drug (206) is slowly released.

Morphology of Nanofibers

Morphology and diameter of nanofibers were studied by secondary electron microscope (SEM, FEI Nova NanoSEM 450). To visualize the effect of bacterial activity on degradation of nanofibers, fibers were immersed in bacterial supernatant solution and Tryptone Soya broth (TSB) for 72 h, and observed them under SEM. 18 h cultured bacteria ($10^8$ CFU $mL^{-1}$) were used to prepare the supernatant. The supernatant was centrifuged from 18 h culture (5000 rpm for 15 min) and then filter-sterilized (0.22 μm filters) before storage at 4° C.

The core-shell structure of the prepared nanofibers was characterized by transmission electron microscopy (JEOL JEM-2100F) at an accelerating voltage of 200 kV, for which carbon-coated copper grids were used to collect the nanofibers.

Drug Release Measurement

To study the drug release, nanofibers were immersed in bacterial supernatant and TSB (4 mg in 2 mL media) and incubated at 37° C. To obtain the cumulative release of BTAC, 600 μL of eluted drug medium was removed for quantification; this volume replaced with fresh supernatant to provide sink conditions. Removed media was mixed with 0.25 mL orange II dye solution. After 5 min, 600 μL chloroform was added to the dye-BTAC complex, and the mixture was vortexed for 45 s to ensure that the chloroform and dye were mixed thoroughly. 600 μL of the chloroform phase (the bottom layer) was removed into a UV silica cuvette, and the absorbance was measured at 485 nm. The structures of (a) orange II dye and (b) BTAC are shown below.

(a)

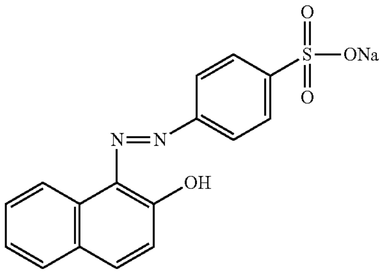

Orange II dye (b)

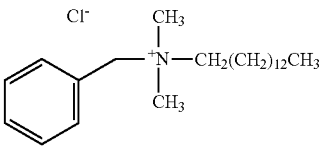

BTAC

Antibacterial Test

The antibacterial activity of the nanofiber mats was tested by colony counting method against *Staphylococcus aureus* (*S. aureus*) and *E. coli*, which are commonly found on burn wounds. For the antibacterial studies, logarithmic-phase cultures were prepared by initially suspending several colonies in phosphate buffered saline (PBS, 0.1 M, pH 7.4) at a density equivalent to a 0.5 McFarland standard of $1\times10^8$ colony forming units (CFU) mL=$^1$ and then diluted 100 times to $1\times10^6$ CFU $mL^{-1}$. 15 μL of the diluted *E-coli* and *S. aureus* suspension was further diluted into 45 mL cation-supplemented MuellerHinton (MH) broth and TSB, respectively. After culturing in the incubator at 37° C. for overnight, the concentration of bacteria went up to $10^8$ CFU $mL^{-1}$.

2 mL of bacteria suspension was added to 4 mg of nanofibers and incubated. At the predetermined contact times, 150 μL of bacteria culture was taken from the flask, neutralized, and decimal serial dilutions with PBS were repeated with each initial sample. 30 μL of the diluted sample was then spread onto four zones of a Tryptone Soya agar plate (CM 0131, OXOID). After incubation of the plates at 37° C. for 18 h, the number of viable bacteria (colonies) was counted manually for control (A, bacteria suspension without sample) and BTAC-loaded nanofibers (B). Bacteria reduction was reported as percentage and Log 10. The percentage reduction of bacteria (%)=(A−B)/A×100; and logarithm reduction=log (A/B).

Cytotoxicity Tests

An in vitro cytotoxicity assay was conducted on fibroblast cells (ATCC-PCS-201 neonatal human dermal fibroblast) to evaluate the effect of drug-loaded nanofibers. Nanofibers were cut in to the same shape and weighted to 4 mg (triplicate). They were pre-soaked in 1 mL of ethanol for 10 min. Samples were exposed to UV light for 45 min (each side). Fibroblast cells were cultured in 24 well-plates at density of $1\times10^5$ (cell/mL). After reaching to 90% confluence, 2 mL of fibroblast culture medium was added to each of the wells and the dressings. Afterwards, the cells were incubated at 37° C. for 24 h. Cell viability was determined using MTT assay after removal of dressings. Each well received 500 μL of 1:10 (v/v) MTT and fibroblast medium solution. Subsequently, after 2 h incubation at 37° C., the culture medium with the MTT solution were aspirated and replaced by 500 μL DMSO. Finally, 100 μL aliquots from each well (in triplicate) were transferred to 96-well plates and viability of cells was evaluated using spectrophotometer at 570 nm wavelength (PowerWave™ XS2 Microplate Spectrophotometer, BioTek Instruments Inc., Canada).

Results and Discussion.

In summary, the BTAC-loaded core-shell nanofibers significantly inhibited *Staphylococcus aureus* and *Escherichia coli* growth over 2 hours. The core-shell structure provided the more controlled release of BTAC and prolonged antibacterial properties, as compared to single nanofibers. The core-shell nanofibers exhibited minimal cytotoxicity against fibroblast cells, with greater than 80% viable cells remaining after 24 hours of contact. The tested core-shell nanofibers can be used for on-demand release of antibacterial agents effective against lipase-secreting bacteria.

The exceptional properties of these bacteria responsive core-shell nanofibers, which degraded in response to the presence of bacteria, can provide on-demand biocide release. Core-shell nanofibers are capable of a controllable release, and can provide efficient and prolonged bacterial killing activity as needed, when bacteria are present. However, the delay in the initiation of release until such bacteria are present provides an advantage that no antibacterial agent is deployed when it is not needed. The selective release of antibacterial agent from the core-shell nanofibers permitted the exposed fibroblast cells to maintain high cell viability. Efficient antibacterial activity of nanofibers, without comprising wound healing, makes core-shell nanofibers advantageous systems to approach a reduction in wound infections.

Morphology of Electrospun Nanofibers

SEM photos were taken to study the morphology of nanofibers.

Figure 3:
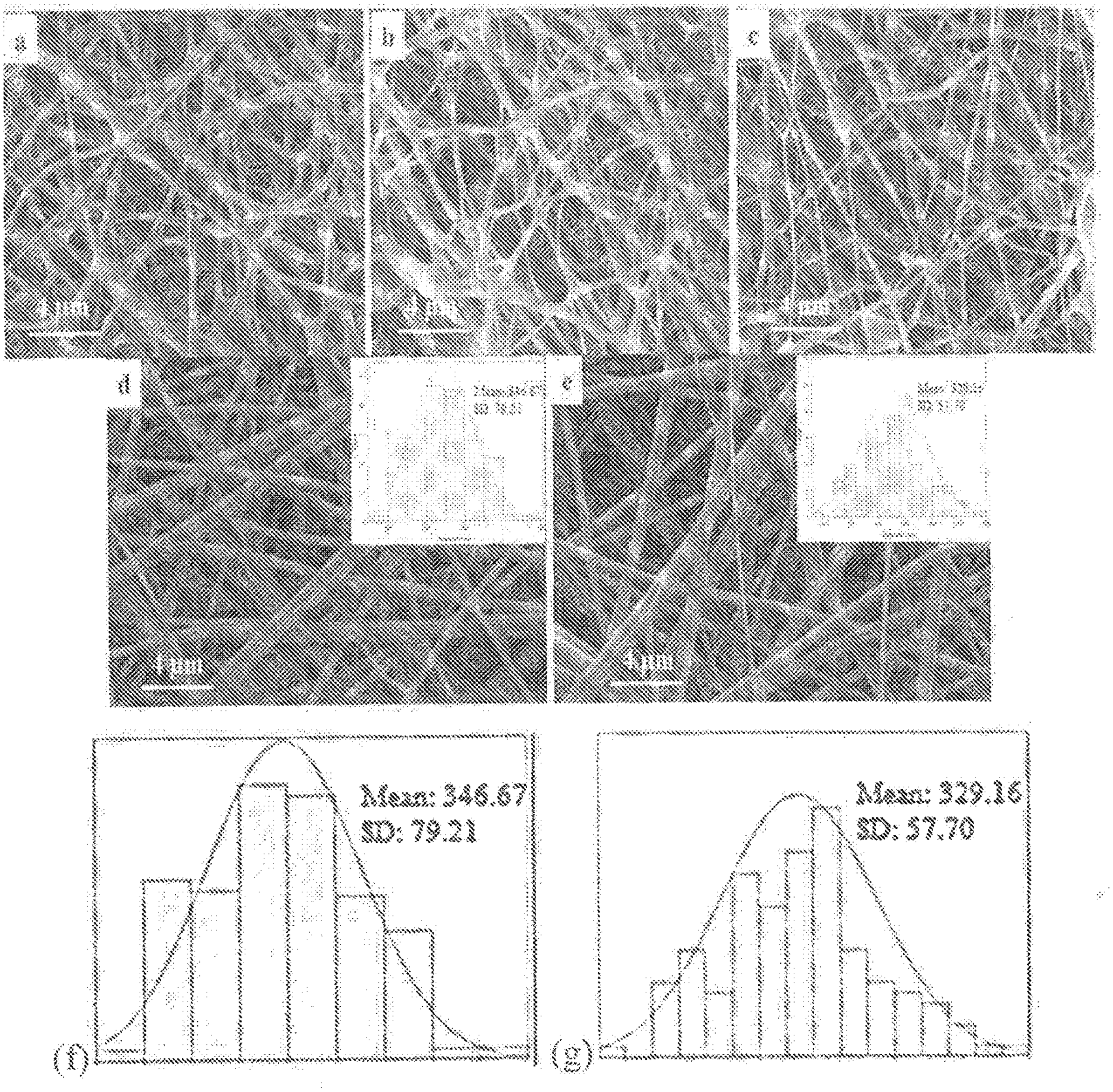
FIG. 3 shows the morphology of nanofibers with different ratios of PCL:PES in Panels (a) to (c); different CS/PCL-PES or S/PCL-PES values in Panels (d) and (e); and distribution curve of fiber diameter in Panels (f) and (g).

FIG. 3 shows the morphology of nanofibers with different ratios of PCL. Panel (a) shows PCL:PES 5:1; Panel (b) shows PCL:PES 2:1; Panel (c) shows PCL-PES 1:1; Panel (d) shows CS/PCL-PES (30%)/1:1/2.5% BTAC; Panel (e) shows S/PCL-PES (30%)/1:1/2.5% BTAC. Panel (f) shows a larger version of the inset distribution curve of panel (d) showing a mean diameter of 346 nm (+79.21 SD); and Panel (g) shows a larger version of the inset distribution curve of panel (e) showing a mean diameter of 329.16 nm (+57.70 SD).

The PES solution that was used in the nanofibers had 20% primary concentration. All the ratios reflected the merged morphology. FIG. 3, Panel (c) that related to PCL-PES 1:1, had a higher ratio of PES than other samples. Due to relatively lower molecular weight of PES than PCL, the higher the amount of PES in the polymer solution resulted in lower spinnability and more beads.

Increasing the concentration of PES from 20% to 30% caused a significant changed in the morphology of the nanofibers. As can be seen in the FIG. 1, Panel (d) and Panel (e), the morphology of core-shell and single nanofibers changed from bead-and-string to a completely fibrous structure. A 1:1 ratio for PCL:PES is preferable to other ratios, because of higher degradability of PES than PCL. Thus, this concentration and ratio were maintained in all of the following experiments.

Both single and core-shell drug-loaded nanofibers showed a nano-sized diameter. As it was expected, core-shell nanofibers had a slightly higher diameter (346 nm) than single ones (329 nm), because of higher syringe internal diameter (inner diameter for shell in core-shell syringe: 1.2 mm; and for single syringe: 0.8 mm).

To confirm the core-shell structure of nanofibers, TEM photos of drug loaded nanofibers (shell: PCL/PES, core: PVP/2.5% BTAC) were taken. To prepare the sample, polymer solution was directly electrospun on carbon coated cupper grids. The micrographs clearly showed the core-shell structure of nanofibers. A sharp boundary between shell and core along the length of the fiber was present, which was due to different viscosity of core and shell solution and partial-immiscibility. The presence of nitrogen in PVP and BTAC could enhance the TEM contrast over that of PCL/PES.

Figure 4:
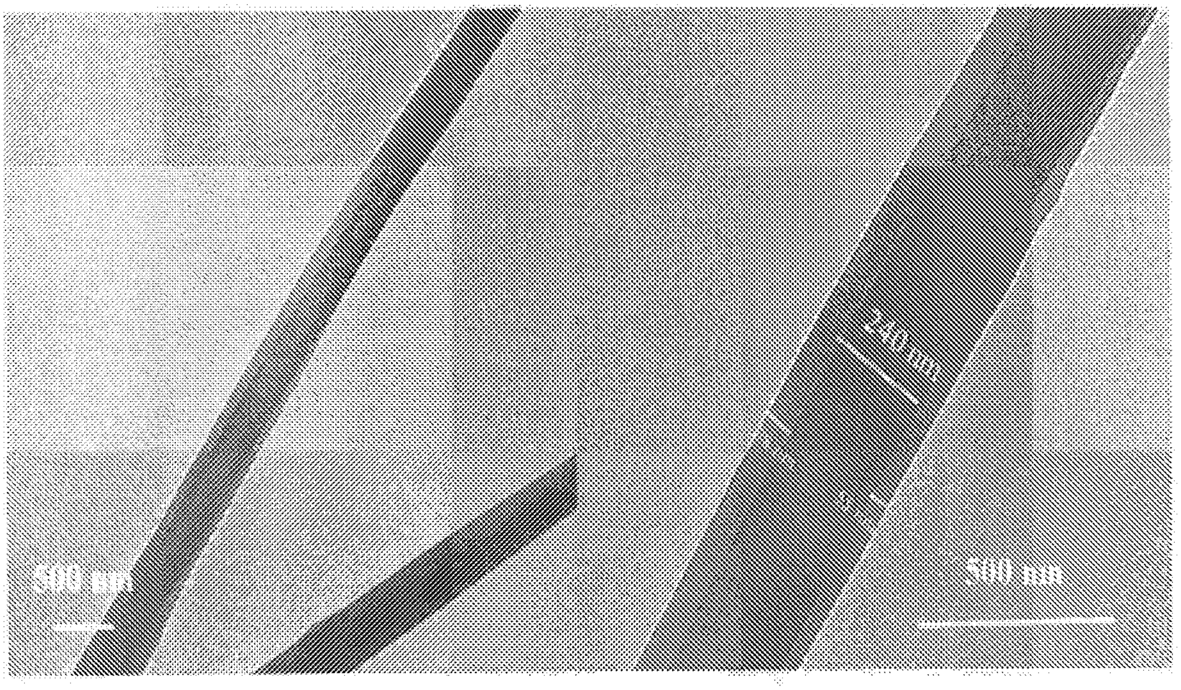
FIG. 4 shows two exemplary TEM photos of the drug loaded antibacterial nanofiber.

FIG. 4 shows two exemplary TEM photos of the drug loaded antibacterial nanofiber (shell: PCL/PES, core: PVP, 2.5% BTAC), with the right side photo being more highly magnified than the left side photo.

To better understand the effect of PES on the degradation, nanofibers were immersed in TSB and bacterial supernatant for 72 h and were studied using SEM photos. Different degradability of PCL and PES could be observed.

Figure 5:
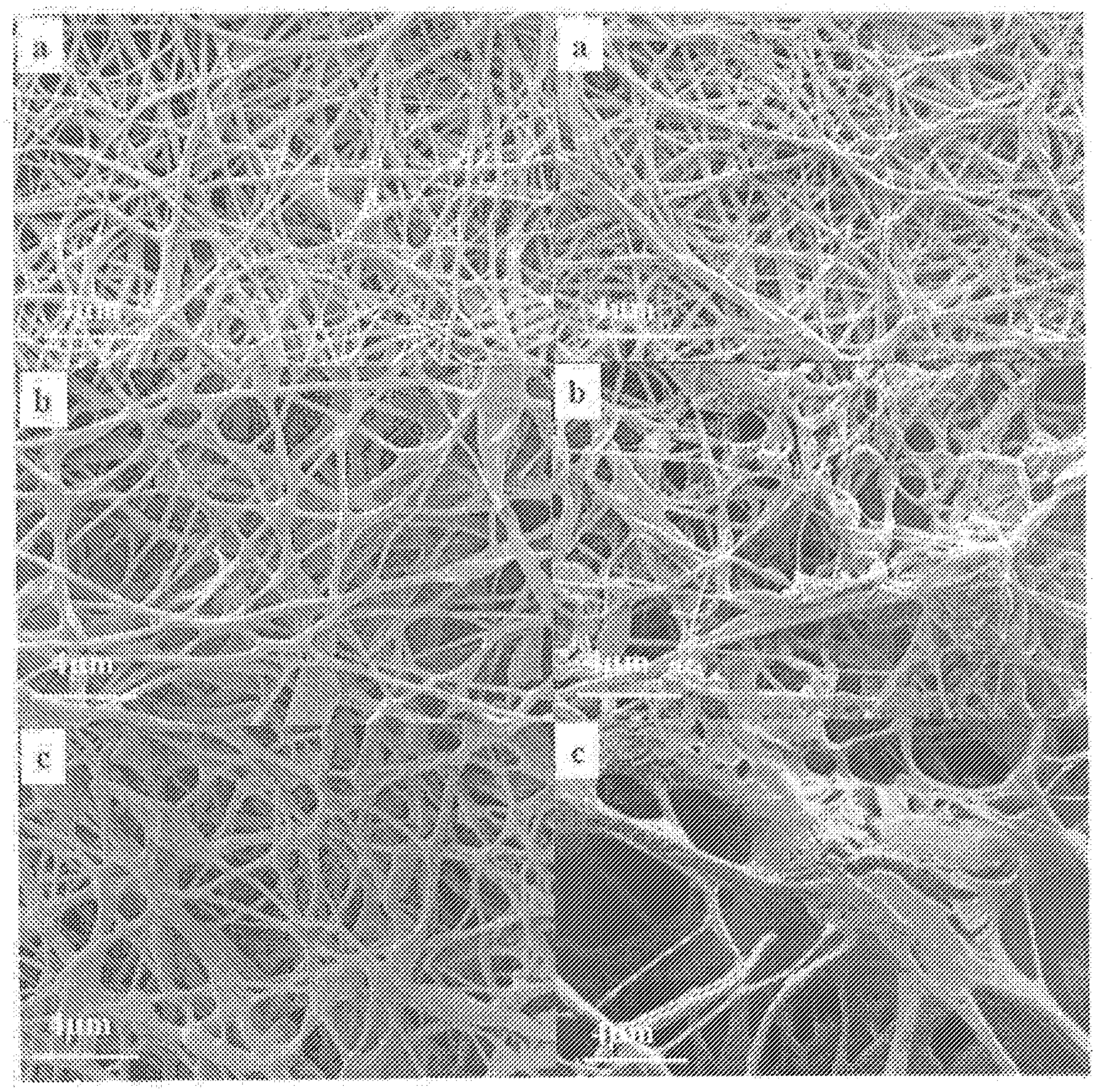
FIG. 5 illustrates the morphology of nanofibers immersed in TSB (left-side) and supernatant (right-side) during 72 h; Panel (a) shows PCL, Panel (b) shows S/PCL:PES, and Panel (c) shows CS/PCL: PES.

FIG. 5 illustrates the morphology of nanofibers immersed in TSB (left-side) and supernatant (right-side) during 72 h; Panel (a) shows PCL, Panel (b) shows S/PCL:PES, and Panel (c) shows CS/PCL: PES.

Different degradability of PCL and PES is emphasized by comparison of Panels (a) and (b). Nanofibers containing PES showed higher disintegration than PCL after immersion in media. That was the reason that we chose the nanofibers with higher ratio of PES (1:1). On the other hand, bacterial supernatant had significant impact on degradation of nanofibers containing PES. Bacterial activity caused enzymatic degradation of ester linkage in the PES nanofibers. This observation was consistent with the study by Hoang et al., (2007) which compared enzymatic biodegradation of PES, PCL, and poly (3-hydroxybutyrate) (PHB) in the form of films. PES films showed rough surfaces and small cracks in the inoculated culture after 2 days. PHB and PCL films were degraded within 6 days, however the rate of their degradation was lower than PES.

Drug Release Measurements

Nanofibers were immersed in bacteria supernatant and TSB and their drug release was measured using spectrophotometry method during 24 h.

Figure 6:
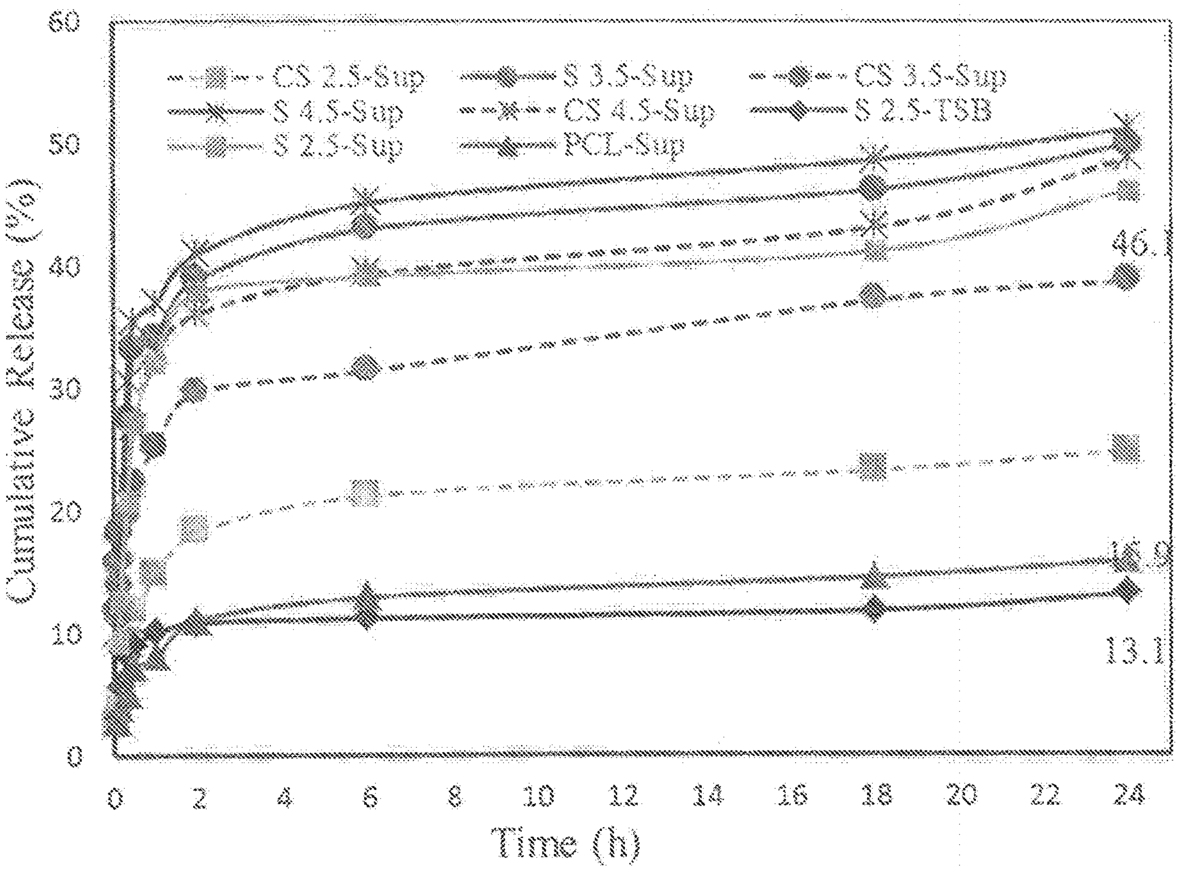
FIG. 6 shows the cumulative release of single and core-shell nanofibers.

FIG. 6 shows the cumulative release of single and core-shell nanofibers (solid lines: single nanofibers, dash lines: core-shell nano-fibers), illustrating that the release of BTAC in TSB (13.1% for S 2.5) is much lower than release in bacteria supernatant (46.1% for S 2.5), which was due to bacterial activity (P-value: 0.0001). Besides, comparison of cumulative release between PCL 2.5 (15.9%) and S 2.5 (46.1%) in supernatant significantly showed the role of PES in the degradation. S 2.5 was fabricated through blending the PCL and PES with 1:1 blend ratio. This results were consistent with degradation study by SEM. Higher degradation rate of PES than PCL, significantly affected the cumulative release of BTAC. It is worthy of mention that all the core-shell nanofibers displayed less cumulative release percentage than single equivalents, which mostly related to lower burst release in the first 2 h.

The slow release was due to the fact in the core-shell nanofiber release was dependent on both degradation of the shell in presence of enzyme and dissolution of PVP as the matrix polymer in the core. In addition, more controllable release in core-shell nanofibers compared to single nanofibers was obvious in the first 2 h. less burst release for CS 2.5 could be observed than S 2.5 (the slope of graph is lower in the first 2 h). This controllable release could cause later depletion of BTAC. This observation indicated effective encapsulation of BTAC into the core. Core-shell nanofibers could keep the antibacterial properties for longer time. This feature also could decrease the cost associated with wound healing. The core-shell structure alleviates the initial burst release and prolongs the release period. However, for single nanofibers formed using a traditional blending electrospinning system, the drug was simply incorporated into ultrafine fibers by dispersing particles into the polymer solution directly. Thus, the agents might migrate fast to the surface or near the surface of the fibers during the electrospinning process, which would lead to severe initial burst release of the loaded drugs. The severe burst release then could lead to excessive initial drug delivery and affect long term antibacterial properties.

Antibacterial Activity

The design of an antimicrobial and biocompatible wound dressing was evaluated. BTAC was chosen from among many possible antibacterial compounds for use in the present Example. Quaternary ammonium (QA) salts are well-known as efficacious biocides against microorganisms including bacteria, and fungi. Given their amphiphilic nature, QACs demonstrate a detergent-like mechanism of action against microbial life. Electrostatic interactions between the positively charged QAC head and the negatively charged bacterial cellular membrane are followed by permeation of the QAC side chains into the intramembrane region, ultimately leading to leakage of cytoplasmic material and cellular lysis.

Table 2 and Table 3 show the antibacterial efficacy of the nanofiber with different formulations against *S. aureus* and *E. coli* with ~8 Log CFU/mL concentration.

TABLE 2

Antibacterial activity of *S. aureus* against nanofibers with different formulations and different contact times.

| Contact time (min) | | 5 | 10 | 20 | 30 | 60 | 120 |
|---|---|---|---|---|---|---|---|
| CS 2.5 | % | 45.7 ± 3.7 | 61.6 ± 4.7 | — | 82.8 ± 3.9 | 96.1 ± 1.0 | 97.9 ± 0.3 |
| | $Log_{10}$ | | | | | 1.4 ± 0.2 | 6.6 ± 0.3 |
| S 2.5 | % | 67.3 ± 8.5 | 88.7 ± 1.7 | — | 94.6 ± 3.0 | 97.6 ± 0.8 | 100.0 |
| | $Log_{10}$ | | | | | 1.6 ± 0.3 | 8.8 |
| CS 3.5 | % | 78.4 ± 6.9 | 88.3 ± 1.5 | — | 99.5 ± 0.5 | 99.9 ± 0.1 | 100.0 |
| | $Log_{10}$ | | | | 2.1 ± 0.2 | 2.9 ± 0.4 | 8.8 |
| S 3.5 | % | 75.3 ± 1.3 | 90.7 ± 0.8 | 99.5 ± 0.8 | 99.7 ± 0.4 | 100.0 | 100.0 |
| | $Log_{10}$ | | | 2.3 ± 0.4 | 2.6 ± 0.3 | 8.8 | 8.8 |
| CS 4.5 | % | 99.6 ± 0.3 | 100.0 | — | | | |
| | $Log_{10}$ | 2.4 ± 0.2 | 8.9 | | | | |

TABLE 2-continued

| Antibacterial activity of *S. aureus* against nanofibers with different formulations and different contact times. | | | | | | | |
|---|---|---|---|---|---|---|---|
| Contact time (min) | | 5 | 10 | 20 | 30 | 60 | 120 |
| S 4.5 | % | 100.0 | — | | | | |
| | $Log_{10}$ | 8.9 | | | | | |
| PCL 2.5 | % | 34.4 ± 6.6 | 47.7 ± 6.8 | 50.4 ± 4.0 | 58.0 ± 2.9 | 65.5 ± 6.6 | 83.9 ± 1.3 |
| | $Log_{10}$ | | | | | | |
| BTAC | % | 96.1 ± 0.2 | 98.5 ± 0.9 | 100.0 | — | | |
| | $Log_{10}$ | 1.4 ± 0.2 | 1.8 ± 0.3 | 8.9 | | | |

TABLE 3

| Antibacterial activity of *E. coli* against nanofibers with different formulations and different contact times. | | | | | | | |
|---|---|---|---|---|---|---|---|
| Contact time (min) | | 5 | 10 | 20 | 30 | 60 | 120 |
| CS 2.5 | % | 7.9 ± 0.9 | 15.5 ± 3.1 | — | 53.0 ± 5.2 | 60.3 ± 5.2 | 96.9 ± 0.5 |
| | $Log_{10}$ | | | | | | 1.5 ± 0.1 |
| S 2.5 | % | 14.9 ± 3.8 | 26.3 ± 3.1 | — | 74.0 ± 2.0 | 78.6 ± 3.6 | 98.9 ± 0.4 |
| | $Log_{10}$ | | | | | | 2 ± 0.1 |
| CS 3.5 | % | 27.2 ± 1.4 | 37.1 ± 1.82 | — | 94.8 ± 0.5 | 95.2 ± 0.4 | 100 |
| | $Log_{10}$ | | | | | 1.3 ± 0.1 | 8.9 |
| S 3.5 | % | 38.9 ± 3.8 | 49.1 ± 3.1 | 61.6 ± 4.2 | 96.3 ± 0.6 | 97.1 ± 0.4 | 100 |
| | $Log_{10}$ | | | | 1.4 ± 0.2 | 1.5 ± 0.1 | 8.9 |
| CS 4.5 | % | 45.9 ± 0.9 | 60.8 ± 3.5 | 70.2 ± 1.7 | 97.0 ± 0.3 | 99.3 ± 0.2 | 100 |
| | $Log_{10}$ | | | | 1.5 ± 0.1 | 2.2 ± 0.3 | 8.9 |
| S 4.5 | % | 57.3 ± 4.3 | 64.9 ± 2.3 | 76.6 ± 3.0 | 97.8 ± 0.1 | 100.0 | 100 |
| | $Log_{10}$ | | | | 1.7 ± 0.0 | 8.9 | 8.9 |
| PCL 2.5 | % | 5.7 ± 2.9 | 12.0 ± 1.8 | 24.0 ± 4.6 | 38.3 ± 6.8 | 48.7 ± 5.6 | 47.8 ± 3.2 |
| | $Log_{10}$ | | | | | | |
| BTAC | % | 95.3 ± 0.3 | 96.0 ± 0.2 | 98.8 ± 0.5 | 100.0 | | |
| | $Log_{10}$ | 1.3 ± 0.0 | 1.4 ± 0.1 | 1.9 ± 0.1 | 8.9 | | |

According to the results, antibacterial activity of the nanofibers progressively increased as the contact time increased. As expected, all the core-shell nanofibers showed less bacteria inhibition than single nanofibers. The hydrophobic nature of the shell (PCL and PES) could effectively retard the penetration of water into the fibers and thereby prolong the release period of BTAC and consequently the antibacterial efficacy. It is worth noting that antibacterial activity of nanofibers against *S. aureus* as Gram-positive bacteria is higher than Gram-negative bacteria (*E. coli*), which is due to outer membrane containing lipopolysaccharides in gram-negative bacteria. Because QACs target the bacterial cell membrane, they can be considered to be broad-spectrum antibiotics though they exhibit markedly increased activity against Gram-positive bacteria. Gram-positive bacteria possess a single phospholipid cellular membrane and a thicker cell wall composed of peptidoglycan, Gram-negative bacteria are encapsulated by two cellular membranes and a rather thin layer of peptidoglycan. It is due to the presence of this second membrane that QACs and other membrane-targeting antiseptics tend to exhibit decreased activity against Gram-negative species.

The antibacterial property of free BTAC was evaluated and compared with the result for BTAC-loaded nanofibers. The concentration of free BTAC was equivalent to cumulative release of S 3.5 within 2 h. S 3.5 obtained 100% bacteria inhibition against *S. aureus* and *E. coli*, within 30 and 120 min, respectively. However, faster bacteria killing activity was observed for free BTAC against both bacteria. Free BTAC obtained 100% bacteria inhibition before 60 min. Thus prolonged and efficient antibacterial properties cannot be expected if free drug is used. This fact is important, when the cytotoxicity results are considered. In addition, the sample PCL 2.5, showed significantly lower Log reduction than S 2.5 (P-value: 0.01). This was due to the absence of PES, which also was mentioned in drug release sections.

Cytotoxicity Test

Optimally, a wound dressing should not release toxic products or produce adverse reactions, which could be evaluated through in vitro cytotoxic tests. One of the most important advantages of bacteria triggered systems is that these systems can reduce possible cytotoxicity by reducing the unneeded release of antibacterial drugs. In the previous section the antibacterial efficacy of the BTAC-loaded nanofibers was analysed. To gain insight into the impact on cell viability of the nanofibers, human dermal fibroblast cells were exposed to membranes. MTT results for dressings within 24 h contact with fibroblast cells are collected and provided in in FIG. 7 and FIG. 8.

Figure 7:
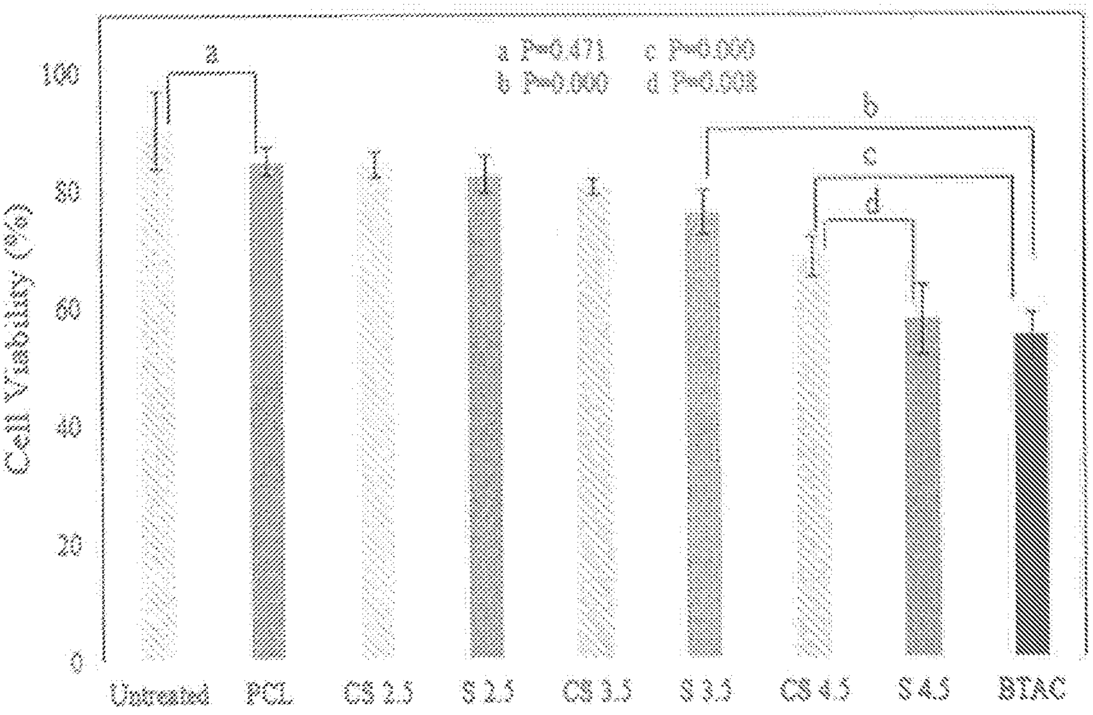
FIG. 7 shows fibroblast cell viability after 24 h of contact with nanofibers.

FIG. 7 shows fibroblast cell viability after 24 h of contact with the nanofibers.

Figure 8:
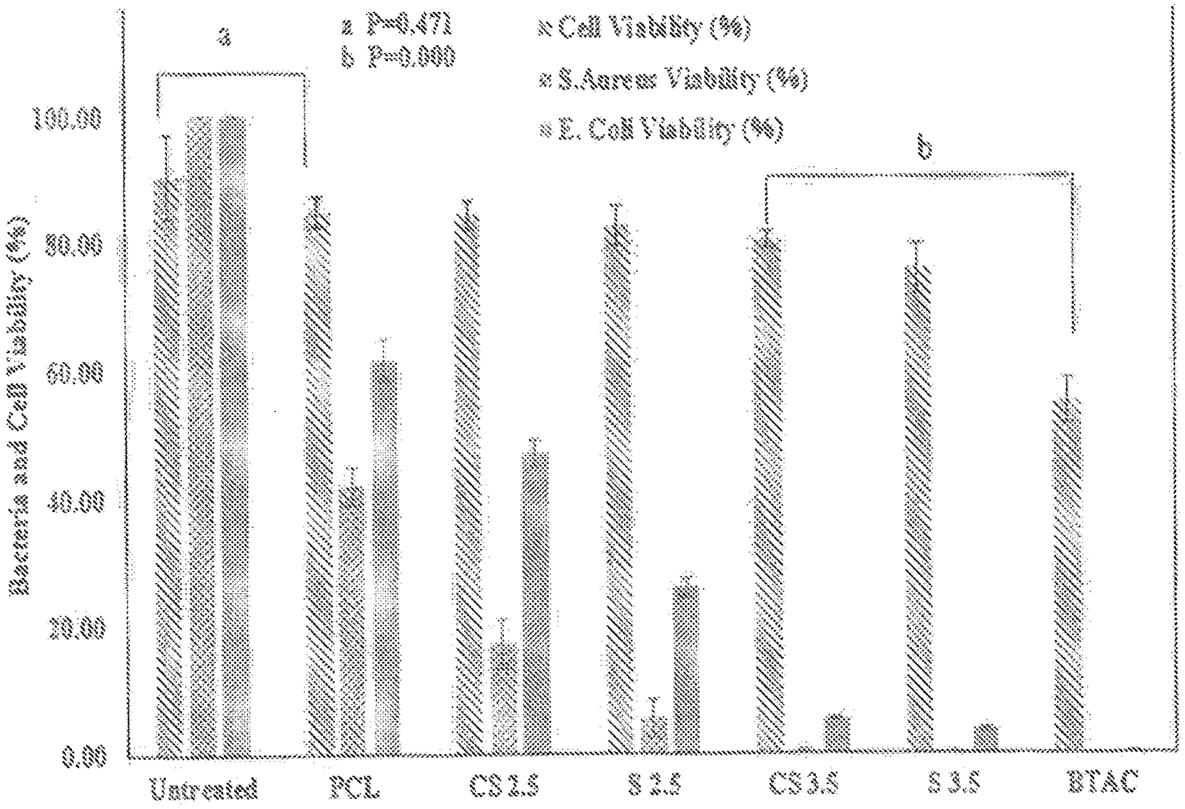
FIG. 8 shows fibroblast, *S. aureus* and *E. coli* viability after 24 h of contact with nanofibers.

FIG. 8 superimposes the data of FIG. 7 for fibroblast cell viability with viability of *S. aureus* and *E. coli* over the same period of time, illustrating the lethal effect of the antibacterial nanofibers on microbes without comparable detriment to the fibroblast cells.

Acceptable viability of cells was recorded for most of the samples with and without BTAC. Untreated nanofiber (CS nanofiber with no drug in the core) showed the highest cell viability. There is no significant difference between cell viability of untreated and PCL nanofibers (P=0.471), which indicated the low release of BTAC in PCL nanofibers. The same result was observed in antibacterial test, when there was a significant difference between antibacterial efficacy of PCL and other samples. This result showed higher degradability of PES in response to bacterial activity.

There was no significant differences between cell viability of single and core shell nanofibers with 2.5% and 3.5% BTAC. However, at higher concentration of BTAC a significant difference between cell viability of S 4.5 and CS 4.5 (P=0.008) was observed.

To compare the cell viability of BTAC-loaded nanofibers and free BTAC, an un-encapsulated BTAC was included in the MTT assay. As nanofibers were in contact with fibroblast cells for 24 h, the concentration of BTAC for MTT assay was chosen to be equivalent to the cumulative release of BTAC from S 3.5 within 24 h (34 mg/L). Cell viability of free BTAC showed a significant difference with S 3.5 and even CS 4.5. The lower cell viability of free BTAC was due to the fact that there was no control on the release. According to FIG. 7, BTAC damages almost half of fibroblast cells (55.2±4.0 compared to 80.5±3.8 for CS 3.5). An aim of the technology is to provide the least cytotoxicity in the wound site. Fibroblasts are critical in supporting normal wound healing, involved in key processes such as breaking down the fibrin clot, creating new extra cellular matrix (ECM) and collagen structures to support the other cells associated with effective wound healing, as well as contracting the wound. Besides, although the free drug showed high antibacterial efficacy in the short time assessed, it would not be efficient over a longer time period, since the drug can be easily washed out by wound exudate. With respect to no obvious cytotoxicity shown in the MTT assay, and strong antibacterial activity toward *S. aureus* and *E. coli* in vitro, CS 3.5 could be utilized in wound dressing for treatment of chronic wounds.

According to the cell vitality results, it can be concluded that drug in the cell media (even in the 24 h) is not at a cytotoxic level. To have a better understanding, the drug release of S 2.5 was measured in the fibroblast cell supernatant within 1 h. As expected, the percentage of cumulative release in the fibroblast supernatant (11.3±0.5) was significantly lower than in bacteria supernatant (32.2±0.8) (P=0.0001). Thus, it can be concluded that fibroblast cell activity does not initiate the degradation of nanofibers. Further, the pH for fibroblast supernatant was 7 and for the bacteria supernatant, the pH was 5.3. The acidic pH of bacterial supernatant could be the other factor that facilitates the degradation. To test this, the percentage of cumulative release of S 2.5 was measure in a pH=5 buffer within 1 h (12.1±0.4), which was significantly higher than TSB (10.1±0.4), but lower than bacteria supernatant. It can be concluded that both the lipase enzyme activity and an acidic pH play role in the degradation of nanofibers.

S 3.5 and CS 3.5 were repeatedly challenged by fresh 8 Log *S. aureus* (29213) for 4 times (each for 2 hours). After 2 hours, samples were washed with PBS, immersed in fresh bacterial suspension, and re-suspended. This re-suspension was repeated twice more for a total of 4 challenges.

Table 4 provides the data obtained from the repeated challenge of the nanofiber membranes.

TABLE 4

Repeated challenge of the nanofiber membranes

| | $1^{st}$ 2 h % | $Log_{10}$ | $2^{nd}$ 2 h % | $Log_{10}$ | $3^{rd}$ 2 h % | $Log_{10}$ | $4^{th}$ 2 h % | $Log_{10}$ |
|---|---|---|---|---|---|---|---|---|
| CS 3.5 | 100.0 | 8.8 | 30 ± 14 | 0.2 | 44.9 ± 7.3 | 0.3 | 50.6 ± 2.1 | 0.3 |
| S 3.5 | 100.0 | 8.8 | 60.6 ± 9 | 0.5 | 21.2 ± 9.9 | 0.1 | 24.7 ± 12.3 | 0.1 |

Figure 9:
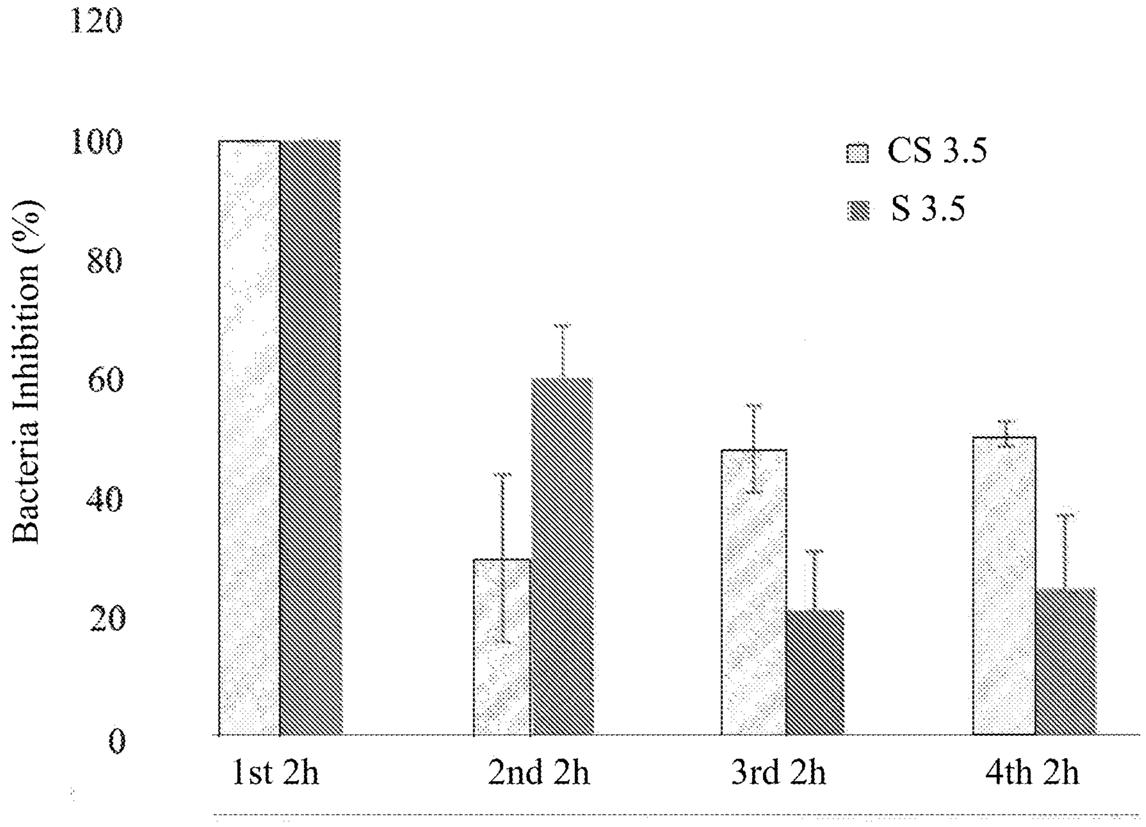
FIG. 9 shows efficacy data after repeated challenge of nanofiber membranes (CS 3.5 and S3.5) with 8 Log *S. aureus* (29213).

FIG. 9 depicts the data of Table 4, showing the repeated challenge of the nanofiber membranes (CS 3.5 and S3.5) with 8 Log *S. aureus* (29213).

Bacteria inhibition of both samples within the first 2 h was 100%. Afterward, the samples were immerse in the new bacteria suspension for the next 2 h, bacteria inhibition of S 3.5 is still higher than CS 3.5 (P=0.033). In the third and fourth repetitions, bacteria inhibition of S 3.5 significantly declined (from 60.6% to 21.2% and 24.7%) and the bacterial reduction by CS 3.5 is significantly higher than S 3.5 (44.9±7.3% versus 21.2±9.9%, p=0.029<0.05; 50.6±2.1% versus 24.7±12.3%, P=0.023<0.05).

The antibacterial efficacy of the core-shell nanofibers was higher than single ones over a prolonged time period, highlighting the advantages of using these fibers in wound healing, and prevention of recurring infections.

Experimental Methods for Highly Sensitive Chromogenic Response

The present invention provides a highly sensitive electrospun polyurethane nanofiber, incorporating a hemicyanine-based chromogenic probe with a labile ester linkage that can be enzymatically cleaved by bacterial lipase released from clinically relevant bacterial strains such as *Pseudomonas aeruginosa* and methicillin-resistant *Staphylococcus aureus* (MRSA). A rapid chromogenic response (color-change) can be achieved by localizing the dye at the surface of core-shell fibers. Sensitivity and rate of response is further increased by incorporating polyvinylpyrrolidone (PVP) dopant in the shell, where the sensitivity can be boosted to enable detection of bacteria at clinically relevant concentrations after 2 h exposure. Electrospinning the color-changing nanofiber produces a fibrous membrane that is responsive to the presence of bacterial lipase.

In one study by the Applicant, a hemicyanine-based dye was synthesized with an ester linkage that can be hydrolyzed by bacterial lipase, resulting in increased intramolecular charge transfer (ICT) between the phenolate ion and hemicyanine group accompanied by a characteristic absorbance shift from 424 nm to 575 nm with a visual color change from yellow to red (Scheme 2). Conjugation of 6-azidohexanoic acid to the hemicyanine derivative provided an azide group for click functionalization of a propargyl polysuccinimide electrospun nanofibrous membrane. However, low conjugation efficiency required a change in strategy to incorporate the dye via blend electrospinning with PU. For the present invention, a new dye, HCy was synthesized by replacing the 6-azidohexanoic acid with hexanoic acid since the azide functional group was no longer required. Chemical structure of the synthesized HCy was confirmed by transmission FTIR, 1H-NMR, 13C NMR and ESI MS. The 1H-NMR spectrum of HCy recorded in CDCl3 showed two 30 triplets (3H and 2H) at 0.97 and 2.62 ppm and one multiplet (4H) at 1.41-1.46 ppm for protons of hexyl chain. The remaining two protons (2H) of hexyl chain emerge with a broad signal at 1.84 ppm that arises due to six protons (6H) of two methyl groups of cyanine moiety. In the aromatic region, NMR showed two doublets (1H and 2H) at 7.02 and 7.27 ppm and one multiplet (3H) at 7.65-7.72 ppm for the protons of the aromatic ring and methylene bridge. The electrospray ionization mass (ESI-MS) spectrum of HCy showed a parent ion peak at (m/z) 400.1651 [M-1]+ corresponding to HCy. Moreover, the FT-IR spectrum of HCy (FIG. 11) showed characterization peaks at (Amax) 2980-2781 (br), 2222, 1770 and 1255 cm-1 corresponding to C—H, C≡N, C═O and C—O stretching, respectively. All these spectroscopic data corroborate 10 the structure HCy for this compound.

Nanofiber Morphology

HCy was incorporated into polyurethane nanofibers by blend electrospinning. Conventional and coaxial methods were implemented to produce dye-loaded fibers with either single or core-shell morphology. PU was used as the primary polymer in the single and core-shell nanofibers to act as a supporting matrix for HCy and add mechanical strength to the dressings. To further boost the sensitivity, the shell of the core-shell nanofibers were doped with PVP at two ratios (2:1 and 4:1 PU:PVP) or with PEG at one ratio (2:1 PU:PEG).

Figure 10:
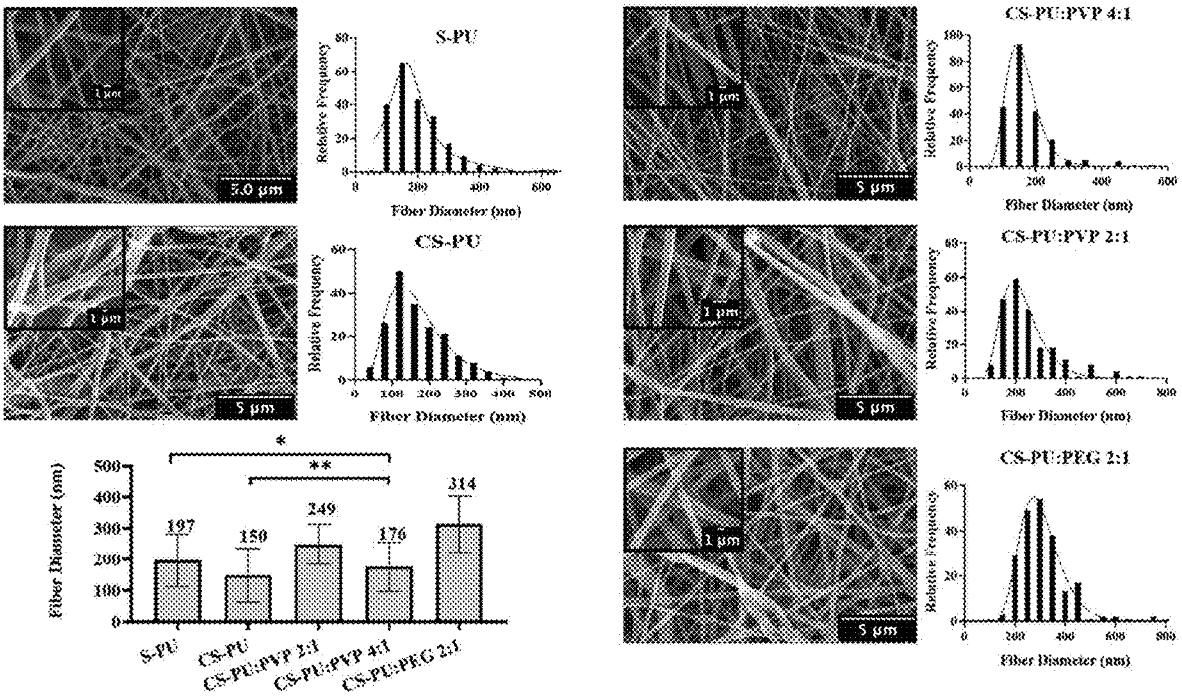
FIG. 10 Shows scanning electron microscopy (SEM) images and size distribution histograms of single and core-shell HCy incorporating nanofibrous membranes (*$p<0.001$,  $p<0.01$,* $p<0.05$—Except the indicated P-value on the graph, P-value of all other differences between samples is ***).

All nanofiber samples had narrow fiber diameter of <320 nm (FIG. 10). CS-PU had a smaller fiber diameter (150±86) than S-PU nanofibers (197±84), likely due to reduced polymer concentration in the core solution of the CS fibers, resulting in thinner overall fiber diameter despite incorporating two solutions. CS formulations with PVP dopant had larger fiber diameter than CS-PU, with the diameter increasing with total shell polymer concentration: CS-PU (7.0%), 150±86<CS-PU:PVP 4:1 (8.75%), 176±79<CS-PU:PVP 2:1 (10.5%) 249±64. All fiber diameters had statistically significant differences in size ($p<0.05$). Smaller fiber diameter could generally be expected to boost the sensitivity of the fibers due to the higher specific surface area and hence higher accessibility of HCy by lipase.

Notably, although the majority of the fibers in each of the electrospun samples had smooth and uniform surface morphology, some beads were visible in the formulations with relatively low total shell polymer concentration: S-PU (7.0%), CS-PU (7.0%) and CS-PU:PVP 4:1 (8.75%). The addition of PVP or PEG at 1:2 ratio with PU eliminated beads from the membranes due to increased concentration and hence viscosity of the polymer solution, resulting in better solution parameters for electrospinning. The obtained bead/fiber fraction through image analyzing showed that for all samples, beads comprised less <10% of the total fiber area. Therefore, although beads could potentially lower the sensitivity due to their low surface area to volume ratio, the effect is assumed to be small and negligible relative to the boosted sensitivity from manipulating other properties of membranes.

Chemical Characterization of Electrospun Membranes

Figure 11:
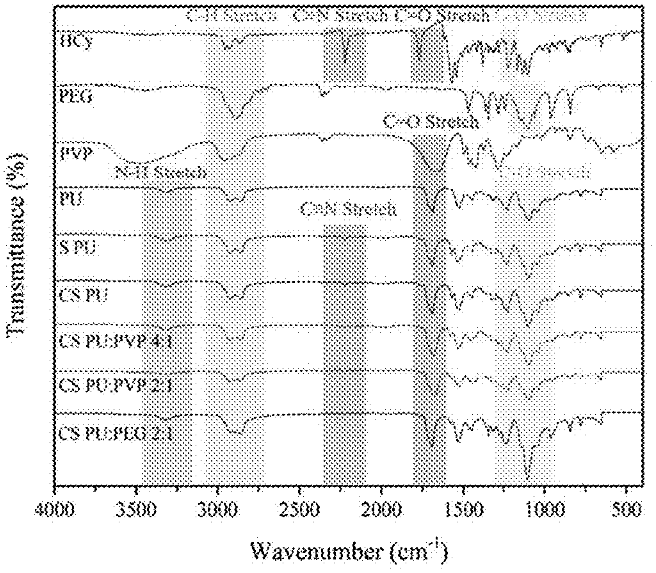
FIG. 11 Shows ATR/FTIR of HCy, polymers and electrospun membranes. HCy, PVP, PEG and PU collected using transmission FTIR; all other samples measured using ATR.

Polymers and HCy powder were characterized by transmission FTIR prior to their incorporation into electrospun membranes (FIG. 11). Membranes containing PU, PVP, PEG and HCy were characterized by ATR-FTIR.

FTIR characterization of HCy yielded the following characteristic peaks: HCy IR max (cm-1): 2980-2781 (C—H stretch), 2222 (C N stretch), 1770 (C═O stretch), 1255 (C—O stretch). The nitrile peak characteristic to the structure of HCy also appeared in the spectra of the electrospun membranes regardless of polymer composition; CS-PU IR max (cm-1): 3319 (N—H stretch), 2980-2781 (C—H stretch), 2224 (C N stretch), 1688 (C═O stretch), 1098 (C—O stretch); CS-PU:PVP 2:1 IR max (cm-1): 3320 (N—H stretch), 2980-2781 (C—H stretch), 2227 (C N stretch), 1682 (C═O stretch), 1098 (C—O stretch); CS-PU:PEG 2:1 IR max (cm-1): 3322 (N—H stretch), 2980-2781 (C—H stretch), 2227 (C N stretch), 1690 (C═O stretch), 1105 (C—O stretch). The appearance of the C N stretch peak close to 2222 cm-1 along with peaks attributable to the functional groups of the constituent polymers in each electrospun membrane confirms successful incorporation of HCy in those membranes. Since PVP contains a T-lactam in its repeating unit, its C═O stretching peak (1660 cm-1) is 20-30 wavenumbers lower and broader than that of PU (1688-1690 cm-1). It is clear from FIG. 11 that all membranes containing PVP give a broader C═O stretching peak with a moderate blue shift in their FTIR spectra.

Colorimetric Response to Lipase

Figure 12:
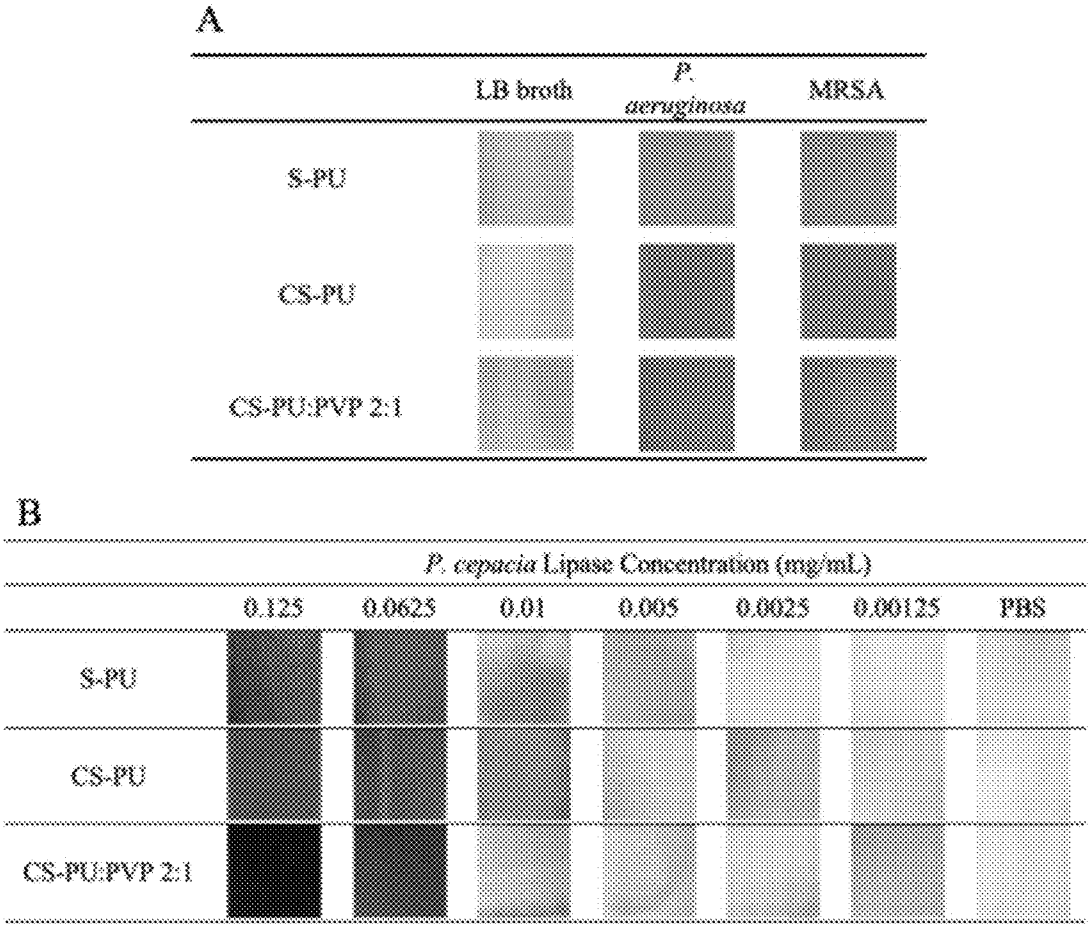
FIG. 12 Shows chromogenic response of S-PU, CS-PU and CS-PU:PVP 2:1 membranes immersed in (A) bacterial supernatants from 104 CFU/mL MRSA (ATCC33592) and *P. aeruginosa* (ATCC 27853) spun down for 15 min at 10,000 g after 24 h immersion for 24 h, and (B) commercial *P. cepacia* lipase for 8 h at various concentrations.

The color changing of S-PU, CS-PU and CS-PU:PVP 2:1 were evaluated in the presence of commercial *P. cepacia* lipase as well as bacterial supernatants to examine the responsiveness of the membranes to lipase without the factor of bacterial growth throughout the duration of the experiment (FIG. 12). Color changing was discernible in supernatant from low concentration 104 CFU/mL MRSA (ATCC 33592) and *P. aeruginosa* (ATCC 27853) after incubation for 24 h, which is clinically relevant since dressings may only be checked for color changing once or twice per day. Furthermore, dressings exposed to commercial lipase from *P. cepacia* were capable of detecting lipase at concentrations as low as 1.25 μg/mL (CS-PU and CS-PU:PVP 2:1) after 8 h. Vivid color changing from yellow to green was exhibited as the lipase concentration was increased, and color change improved with greater exposure time.

Colorimetric Response to Bacteria

Figure 13:
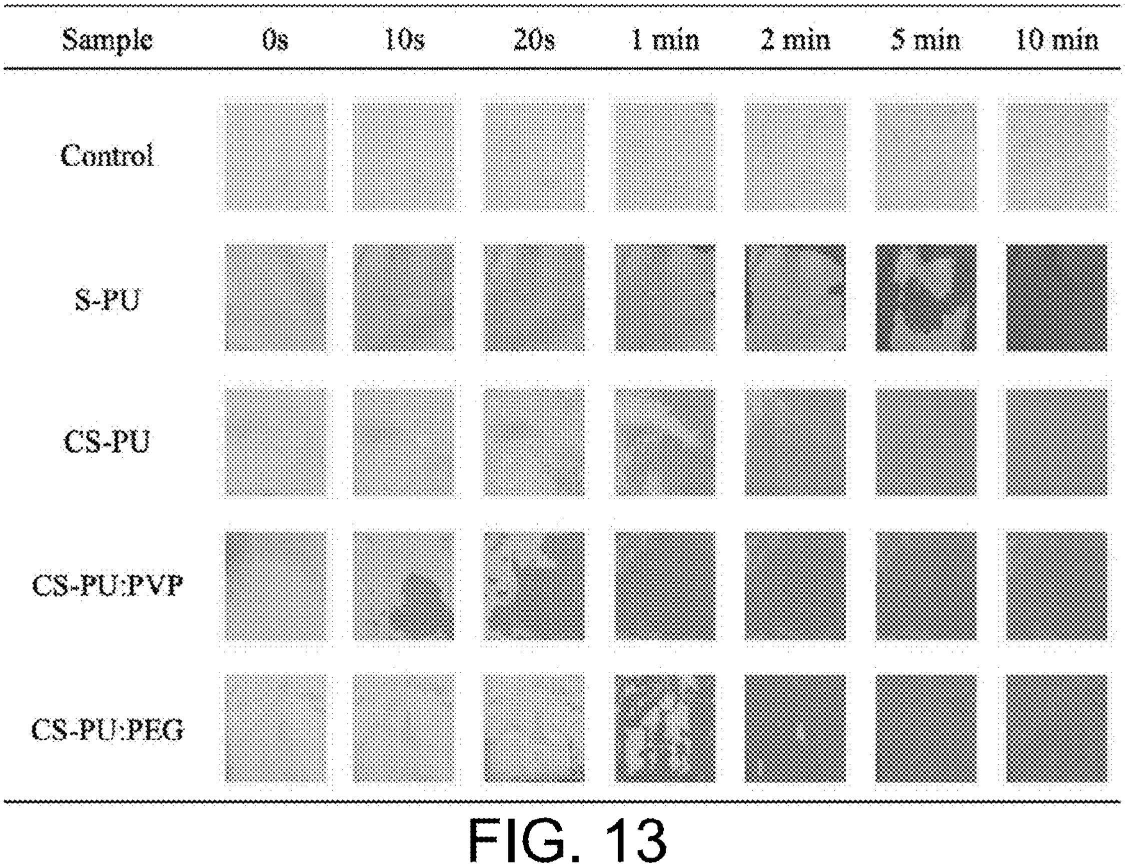
FIG. 13 Shows rate of chromogenic response of HCy containing membranes during incubation with *P. aeruginosa* (ATCC 27853) bacterial lawn (~10×1010 CFU/cm2) for 10 min.

HCy was loaded into the shell of core-shell PU nanofibers to localize the dye at the surface of the fiber to improve accessibility of the dye to lipase. Core-shell nanofibers (CS-PU, CS-PU:PVP and CS-PU:PEG) responded more rapidly to high concentration *P. aeruginosa* lawns than single-electrospun fibers. Fibers with core-shell morphology achieved a uniform color change from yellow to green in <2 min in response to ~$10^{10}$ CFU/$cm^2$ *P. aeruginosa*, in comparison to 10 min required for single-electrospun fibers (FIG. 13). The primary factor contributing to the boosted sensitivity of the CS-PU membrane can be attributed to the enrichment of the surface of the fibers with HCy. Additionally, the statistically significant smaller fiber diameter of CS-PU (150±86 nm) than S-PU (197±84 nm) could contribute to the more rapid response. It should be noted that the darker color of green achieved by the S-PU membrane after 10 minutes exposure to $10\times10^{10}$ CFU/$cm^2$ *P. aeruginosa* arose from its smaller thickness relative to the core-shell membranes. The thicker samples (CS-PU and CS-PU:PVP) required more time to show a dark shade of green on the side that was not in direct contact with agar. However, for samples with the same thickness the color changing response was more intense (darker) for core-shell samples within 2 h. The effect of enriching the shell of the core-shell fibers with HCy was not significant enough to enable the membranes to detect bacteria at a concentration lower than that the single electrospun membranes were sensitive to (~$10^{11}$ CFU/$cm^2$ after 2 h). The core-shell and conventional membranes responded similarly to low concentration lawns with no observable difference in color after 3 h incubation with $2.5\times10^5$ CFU/$cm^2$ *P. aeruginosa* or $1.0\times10^6$ CFU/$cm^2$ MRSA.

Clinically, it is not necessary for a dressing to react immediately as dressings are typically placed on 'clean' wounds and kept in place for 1-2 days. Therefore, it is more critical to detect lower concentrations of bacteria within reasonable periods of time. To improve this detection, we enhanced the sensitivity and presence of color using PVP.

PVP was incorporated into the shell of the core-shell PU nanofibers at two ratios: CS-PU:PVP 4:1 and CS-PU:PVP 2:1. Both the 4:1 and 2:1 PVP fibers exhibited boosted sensitivity, and showed a visible color change from yellow to green after 2 h exposure to 2.5×$10^5$ CFU/cm2 *P. aeruginosa* and 1.0×$10^6$ CFU/$cm^2$ MRSA (FIG. 13). This result indicates that the material is suitable for early detection of wound infection since the clinically relevant threshold of bacterial detection can be considered to range from 5×104-4.6×105 CFU/$cm^2$.

Figure 14:
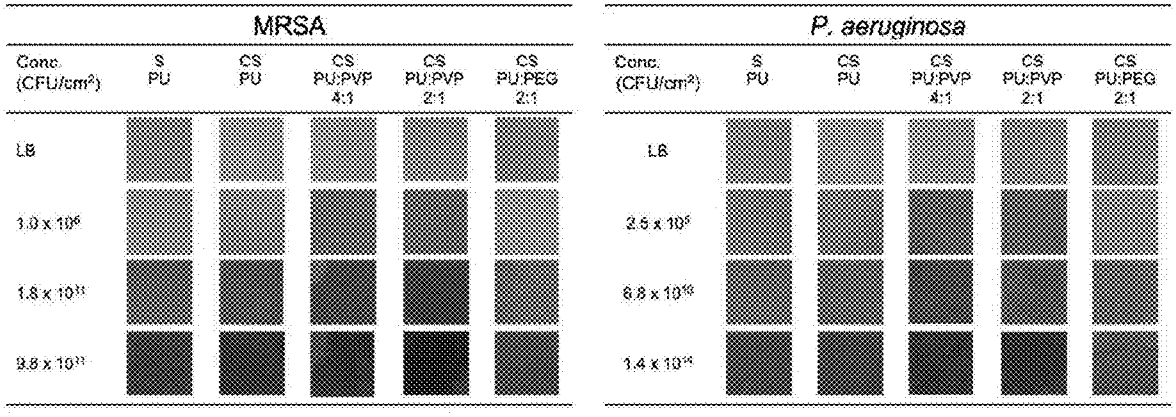
FIG. 14 Shows chromogenic response of HCy containing membranes to *P. aeruginosa* (ATCC 27853) and MRSA (ATCC 33592) after 2 h incubation with bacterial lawns at various concentrations.

Increasing the incubation time (>2 h) or bacterial concentration (>$10^6$ CFU/$cm^2$) demonstrated that PVP also enhanced the discernibility of the color change from yellow to green, as the PVP-containing membranes showed a darker and more vivid green color relative to the S-PU or CS-PU membranes (FIG. 14). Although the addition of PVP to the shell of CS:PU fibers increased the fiber diameter, the negative effects of larger fiber diameter were ultimately outweighed by the beneficial effects of incorporating PVP into the fibers. CS-PU:PEG 2:1 nanofibers did not exhibit boosted sensitivity or enhanced discernibility despite containing a water soluble polymer with similar molecular weight to PVP. Therefore, the role of PVP in enhancing the color changing properties of the nanofibers may not be attributable to pore formation or surface roughness due to the water-soluble polymer being partially dissolved during incubation on moist agar. Rather, the boosted sensitivity likely arises due to the unique properties and structure of PVP.

PVP has been widely used as a dopant in metallic charge transfer complex. Since this polymer has a mesomeric polar γ-lactam structure (Scheme 3), it can facilitate deprotonation of the phenol group of the hydrolyzed HCy, leading to enhanced ICT in the cleaved dye. In addition to facilitating charge transfer, positively charged PVP can form an ionic complex with the cleaved HCy which hence impedes the mobility of cleaved dye. In the samples without PVP (S-PU and CS-PU) the cleaved dye can freely diffuse out of nanofibers to agar while the presence of PVP prevents such movement by forming a complex with the cleaved dye. Therefore, most of the cleaved dye remains within the PVP containing nanofibers, leading to a darker color in comparison to the light and faded green color in PU membranes without PVP (FIG. 14).

Scheme 3. Mesomeric structures of PVP in aqueous environment.

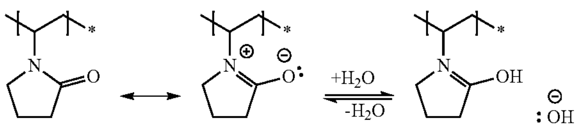

Figure 15:
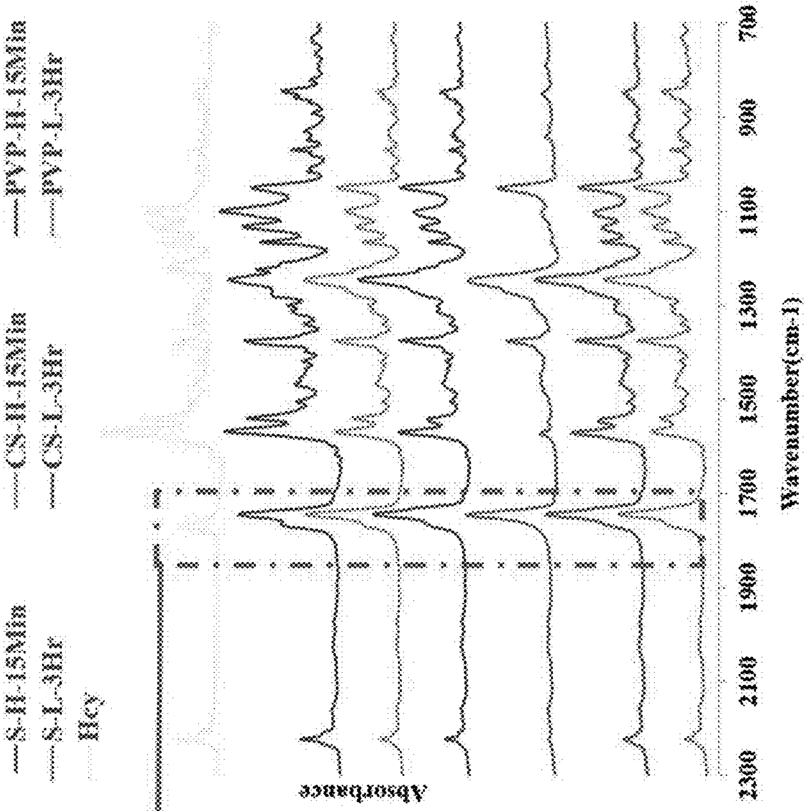
FIG. 15 Shows degree of HCy hydrolysis after 15 min exposure of HCy containing membranes to *P. aeruginosa* (ATCC 27853) lawn (~105 CFU/cm2 or 1010 CFU/cm2).
Figure 15:
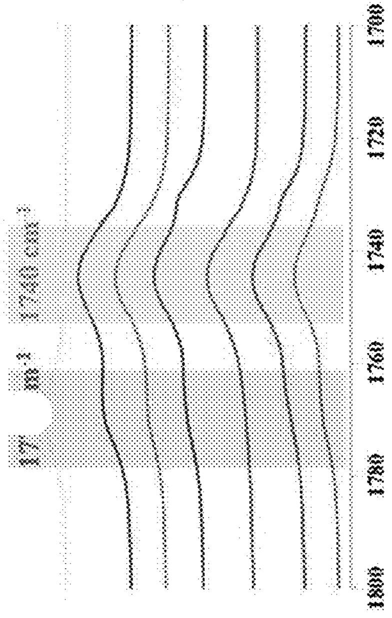
Figure 16:
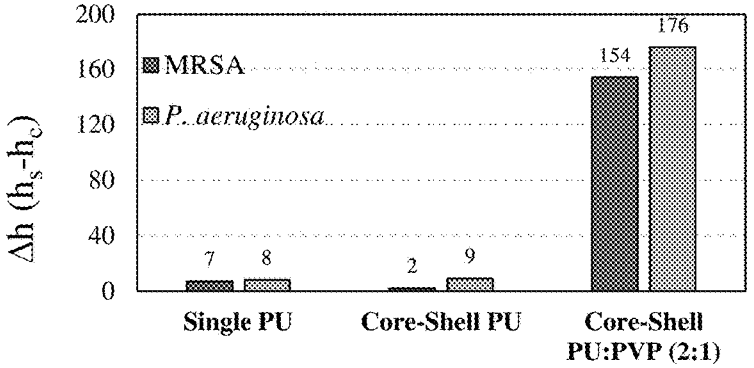
FIG. 16 Shows difference in hue (h) value from CIE L*C*h color space representation of S-PU, CS-PU and CS-PU:PVP 2:1 membranes (hue of sample −4 hue of control) in response to 1.8×1011 CFU/cm2 MRSA (ATCC 33592) or 1.4×1014 CFU/cm2 *P. aeruginosa* (ATCC 27853) bacterial lawns after 3 h incubation.
Figure 17:
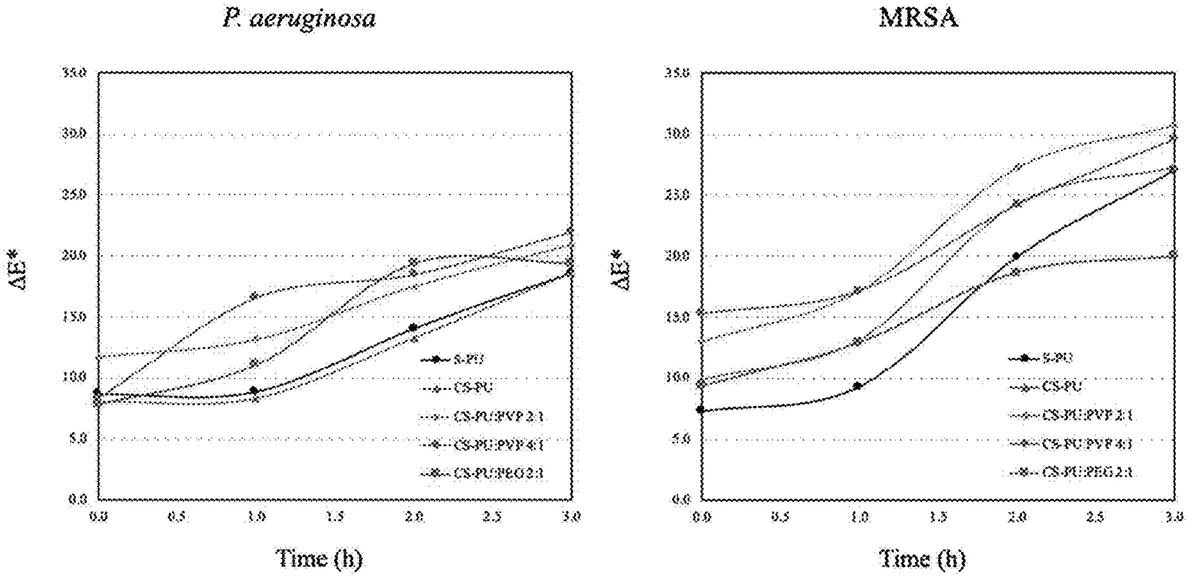
FIG. 17 Shows magnitude of color deviation in CIELAB color space (E*) between bacteria-treated samples and negative control membranes exposed to LB agar without bacteria. Bacterial concentrations were 6.8×1010 CFU/cm2 (*P. aeruginosa* ATCC 27853) and 1.8×1011 CFU/cm2 (MRSA ATCC 33592).

In addition to interacting with the cleaved dye, PVP can affect HCy before cleavage. Acting as a surfactant, hydrophilic PVP can expose more HCy in the interface of lipase and water which leads to higher rate of cleavage. As presented in FIG. 15, FTIR spectra of bacterial samples have a new peak in 1770 cm-1 related to carbonyl group of cleaved by-product hexanoic acid. The peak height ratio of this new peak and the height summation of the original and new carbonyl peaks was computed as an indicator for degree of hydrolysis. Based on the obtained 10 values, CS-PU:PVP 2:1 membrane had higher degree of hydrolysis than S-PU and CS-PU membranes. Incorporation of PVP (CS-PU:PVP 2:1) resulted in an increase of hydrolysis degree by a factor of 1.2× relative to the CS-PU membrane, with 42% hydrolysis after only 3 h exposure to ~$10^5$ CFU/$cm^2$ bacteria lawn (compared to 0% for S-PU membrane and 35% for CS-PU membrane). Increasing the amount of cleaved dye leads to color changing in a lower concentration of bacteria. The color change of bacteria-exposed membranes was also quantified by GretagMacbeth ColorEye® 2180UV spectrophotometer. As shown in FIG. 16, in exposure to either *P. aeruginosa* or MRSA, the presence of PVP leads to a significant increase in CIE L*C*h h value (where h represents the hue angle in the L*C*h colour space). This provides quantitative evidence for more vivid green color changing in the PVP containing membrane since a positive Dh from yellow represents a "less red" or similarly "more green" hue change. Moreover, reflectance spectra were used to calculate CIELAB color space coordinates to quantify the change in color (DE*) relative to membranes exposed to negative control LB agar, where DE*>1 indicates sample membrane color has significantly changed relative to the control. For both *P. aeruginosa* and MRSA, DE* values were consistently higher for PVP-containing membranes than S-PU or CS-PU membranes, indicating a greater magnitude of color change (FIG. 17). After 1 h incubation, the DE* values of CS-PU:PVP 2:1 membrane exceeded those of S-PU by 49.7% and 85.7% for *P. aeruginosa* (6.8×$10^{10}$ CFU/$cm^2$) and MRSA (1.8×$10^{11}$ CFU/$cm^2$) respectively.

Figure 18:
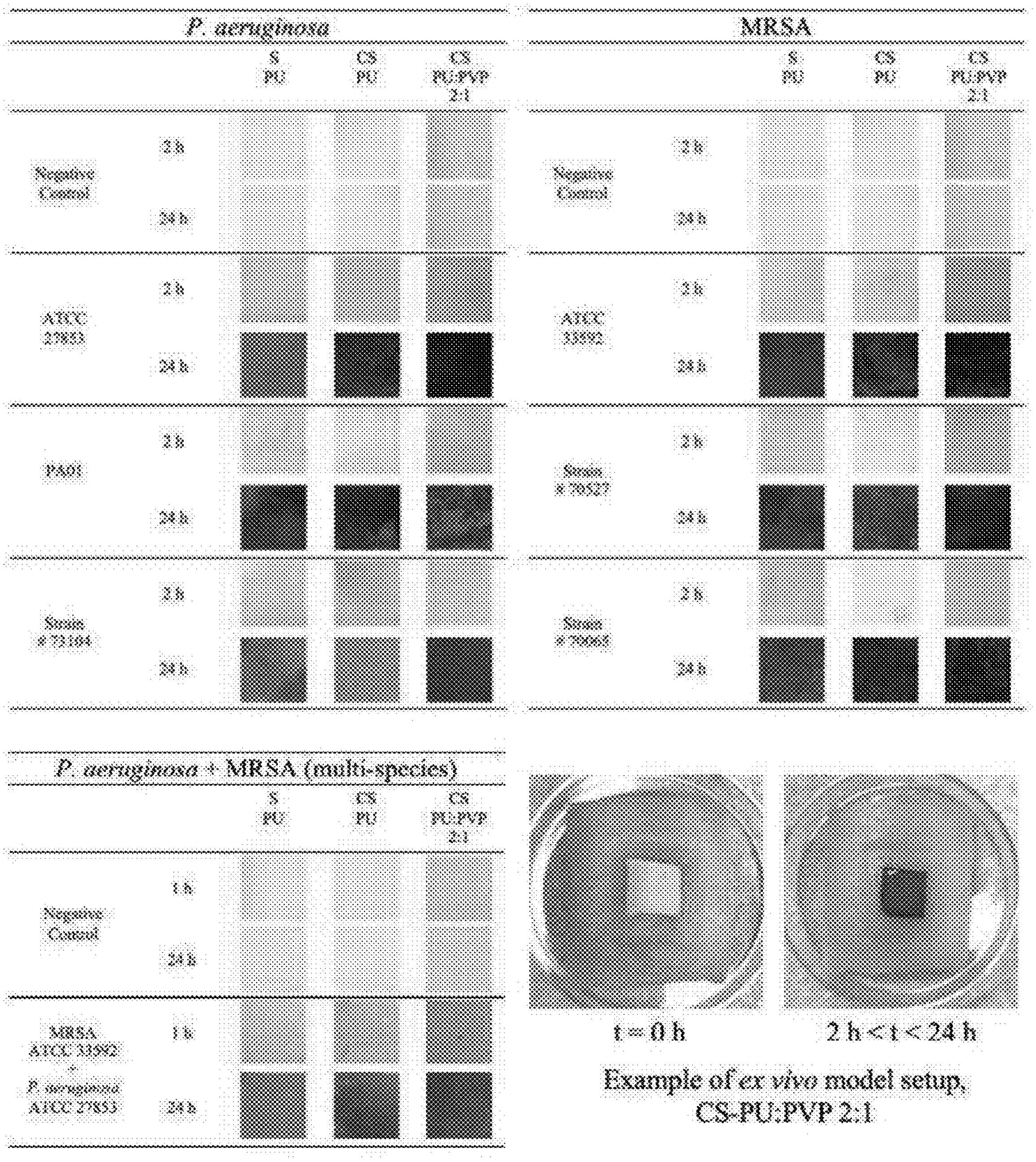
FIG. 18 Shows chromogenic response of HCy containing membranes to MRSA (ATCC 33592, strain #70527 and strain #70065) and *P. aeruginosa* (ATCC 27853, PA01 and strain #73104) on ex vivo pig skin burn wounds. Initial bacterial concentration was in the range of 5.5×106-5.5×107 CFU/cm2 for *P. aeruginosa* strains, and 1.0×107-1.8×108 CFU/cm2 for MRSA strains.
Figure 19:
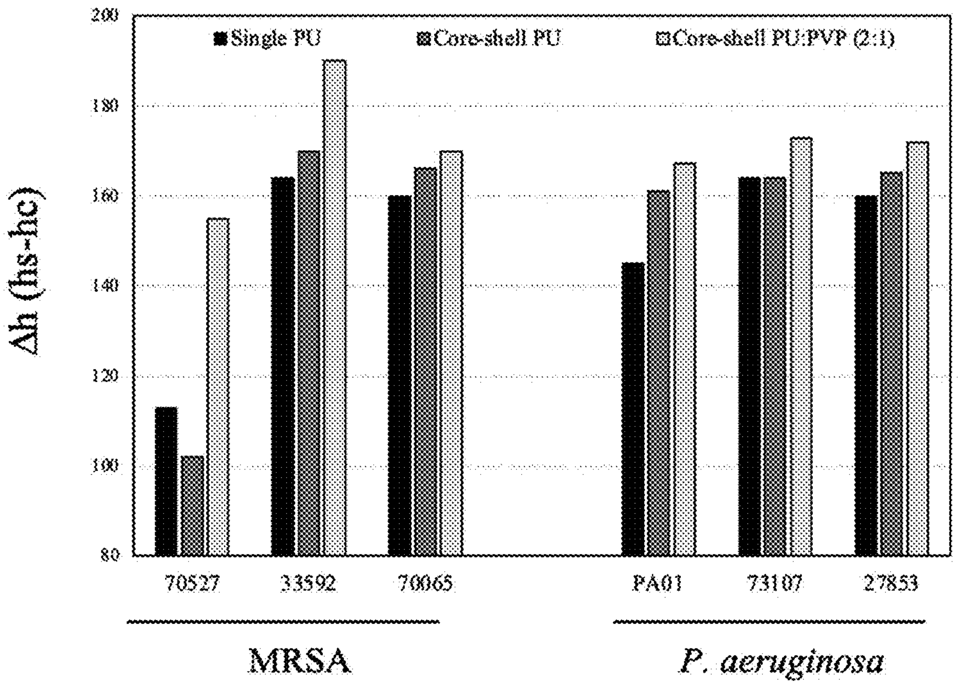
FIG. 19 Shows difference in hue (h) value from CIE L*C*h color space representation of S-PU, CS-PU and CS-PU:PVP 2:1 membranes (hue of sample-hue of control) after 24 h incubation with MRSA (ATCC 33592, strain #70527 and strain #70065) and *P. aeruginosa* (ATCC 27853, PA01 and strain #73104) on ex vivo pig skin burn wounds. Initial bacterial concentration was in the range of 5.5×106-5.5×107 CFU/cm2 for *P. aeruginosa* strains, and 1.0×107-1.8×108 CFU/cm2 for MRSA strains.

Having demonstrated the unique capabilities of PVP to enhance detection of low concentration bacterial lawns on agar, we tested S-PU, CS-PU and CS-PU:PVP 2:1 membranes using an ex vivo porcine burn wound model to examine the response of the membranes to bacteria in a more realistic wound environment (FIG. 18). The bacterial concentration was in the range of 5.5×106-5.5×$10^7$ CFU/$cm^2$ for *P. aeruginosa* strains (ATCC 27853, PA01 and strain #73104), and 1.0×$10^7$-1.8×$10^8$ CFU/$cm^2$ for MRSA strains (ATCC 33592, strain #70527 and strain #70065). The CS-PU:PVP 2:1 exhibited green color changing after 30 min exposure to the wound bed, with a clearly discernible color change from yellow to green after 2 h. CS-PU:PVP 2:1 showed enhanced color changing after 2 h compared to S-PU and CS-PU in all three of the tested MRSA strains as well as two out of three of the tested *P. aeruginosa* strains. Furthermore, the positive change in hue (h) after 24 h was greater for the CS-PU:PVP 2:1 membrane compared to S-PU and CS-PU in all of the six tested bacterial strains, confirming the role of PVP for darker color changing (FIG. 19).

Lipase activity in pig wound beds inoculated with *P. aeruginosa* (ATCC 27853) and MRSA (ATCC 33592) was quantified to demonstrate the relationship between bacterial concentration (CFU/cm2) and lipase activity (nmol/min/$cm^2$). Lipase activity in the wound bed was in the range of 5.5±0.3 to 27±3 nmol/min/$cm^2$ at bacteria concentrations ranging from 7×$10^5$±2×105 to 3×$10^8$±1×$10^6$.

Characterization of Dye Extracted from the Green Membrane

Figure 21:
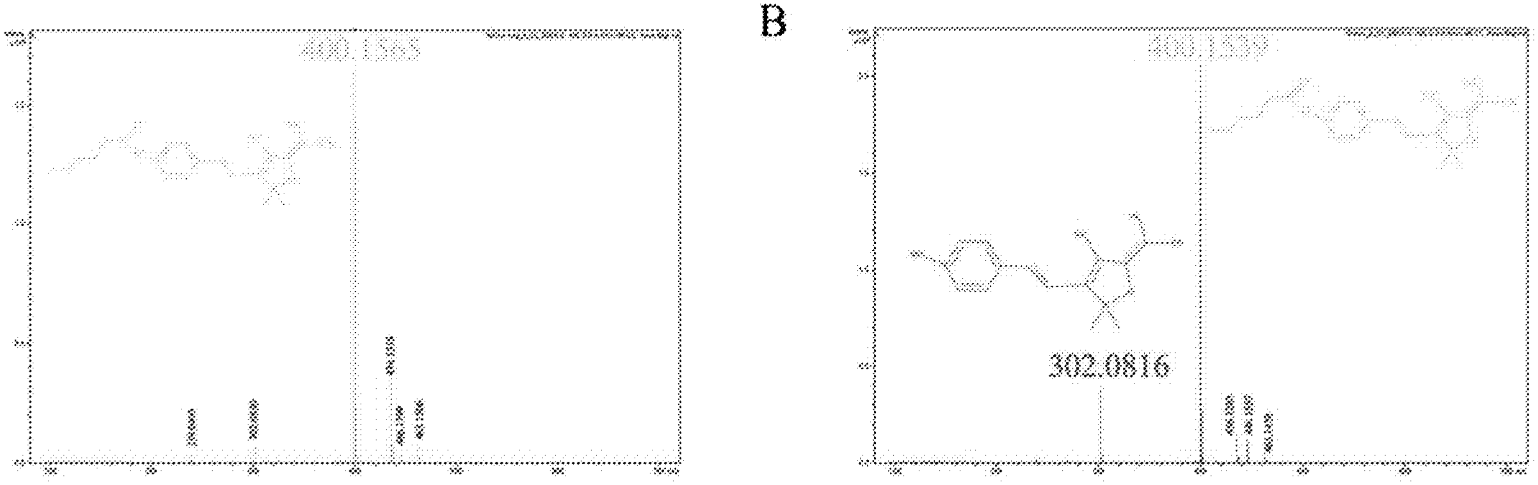
Figure 21:
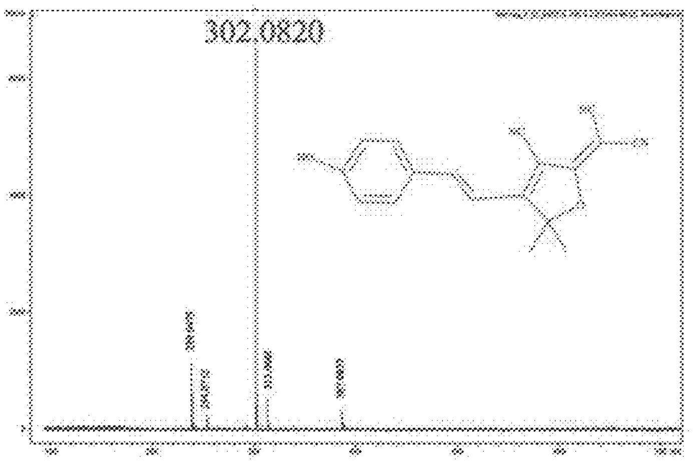

HCy has a bacterial labile ester linkage which experiences cleavage in the presence of lipase. HCy in the cleaved form enjoys an extended conjugated system that leads to color changing from yellow to red (Scheme 2). However, when HCy was incorporated into nanofibers and exposed to bacteria, the observed color changing was green rather than the expected red (FIG. 19). For this reason, we subjected yellow HCy dye, purified red dye and dye extracted from the green CS-PU membrane (without PVP, exposed to $10^{10}$ CFU/$cm^2$ *P. aeruginosa* for 15 min) green extracted dye to mass-spectrometry and ATR-FTIR analyses to gain a better understanding of the unexpected color changing. Yellow dye (C24H23N3O3) had a detected mass of 400.1565 m/z which indicates the synthesis of the dye occurred successfully (FIG. 21-A). For purified red dye (C18H13N3O2), the detected mass was 302.0820 m/z which means purification was properly done and no yellow component remained after hydrolysis (FIG. 21-C). In FIG. 21-A, there is a small peak at 302.0830 m/z which is 4.1% of the abundance of the primary red dye peak at 400.1565 m/z and could be due to hydrolysis induced in the electrospray ionization process. The spectrum of the dye extracted from the green membrane (FIG. 21-B) showed peaks at both 400.1539 m/z and 302.0816 m/z, and the latter has a peak intensity 19% of the 400.1539 m/z peak and could not be attributed to electrospray ionization induced hydrolysis. So, hydrolysis of HCy in membranes upon bacterial contact, as indicated by FTIR spectra presented in FIG. 14, is corroborated by the mass-spectrometry analysis of the extracted dye. We can state that the membrane color change is indeed caused by HCy cleavage and therefore bacteria triggered.

Figure 20:
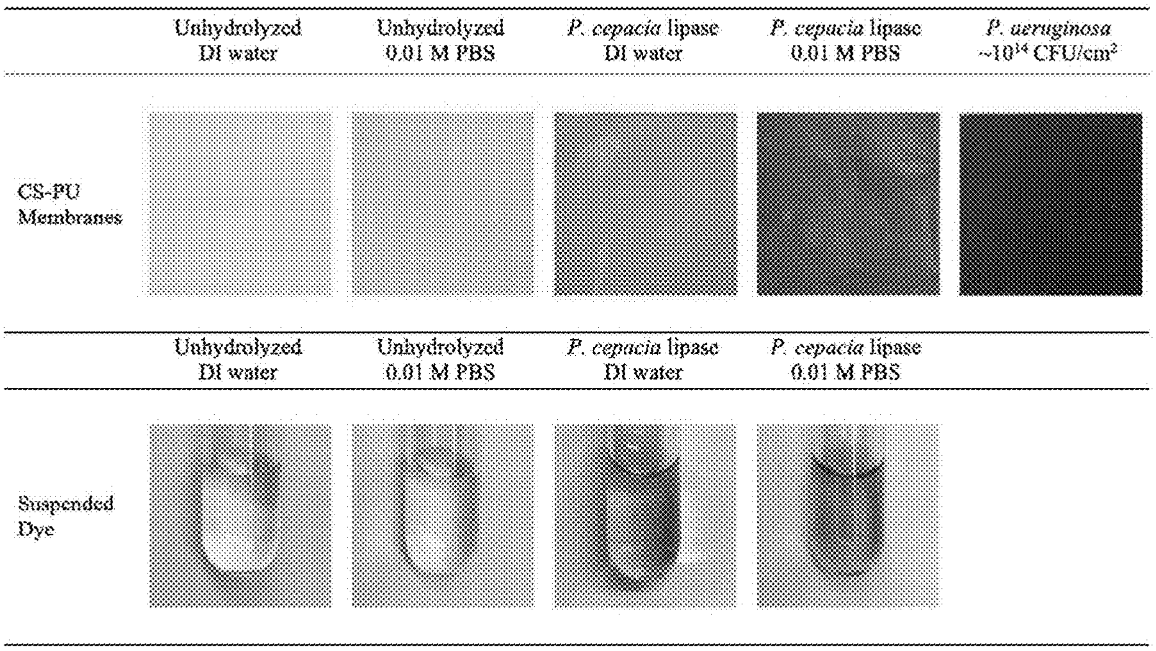
FIG. 20 Shows effect of charge transfer donors (polyurethane and PBS ions) on the chromogenic response of HCy. 50 μM HCy suspended in DI water (5% DMSO) or 0.01 M PBS (5% DMSO) with 0.5 mg/mL commercial *P. cepacia* lipase. 1 cm2 membrane samples contacting ~1014 CFU/cm2 *P. aeruginosa* lawn or immersed in 0.5 mg/mL commercial *P. cepacia* lipase in DI water or 0.01 M PBS FIG. 21. Mass spectra of unhydrolyzed or hydrolyzed HCy in ethyl acetate: (A) HCy, (B) HCy extracted from CS-PU membrane exposed to *P. aeruginosa* lawn (~1010 CFU/cm2) for 15 min, (C) HCy hydrolyzed by commercial *P. cepacia* lipase after separation from yellow dye, (D) Summary of mass spectral data including relative proportion of hydrolyzed red dye in each sample.
Figure 22:
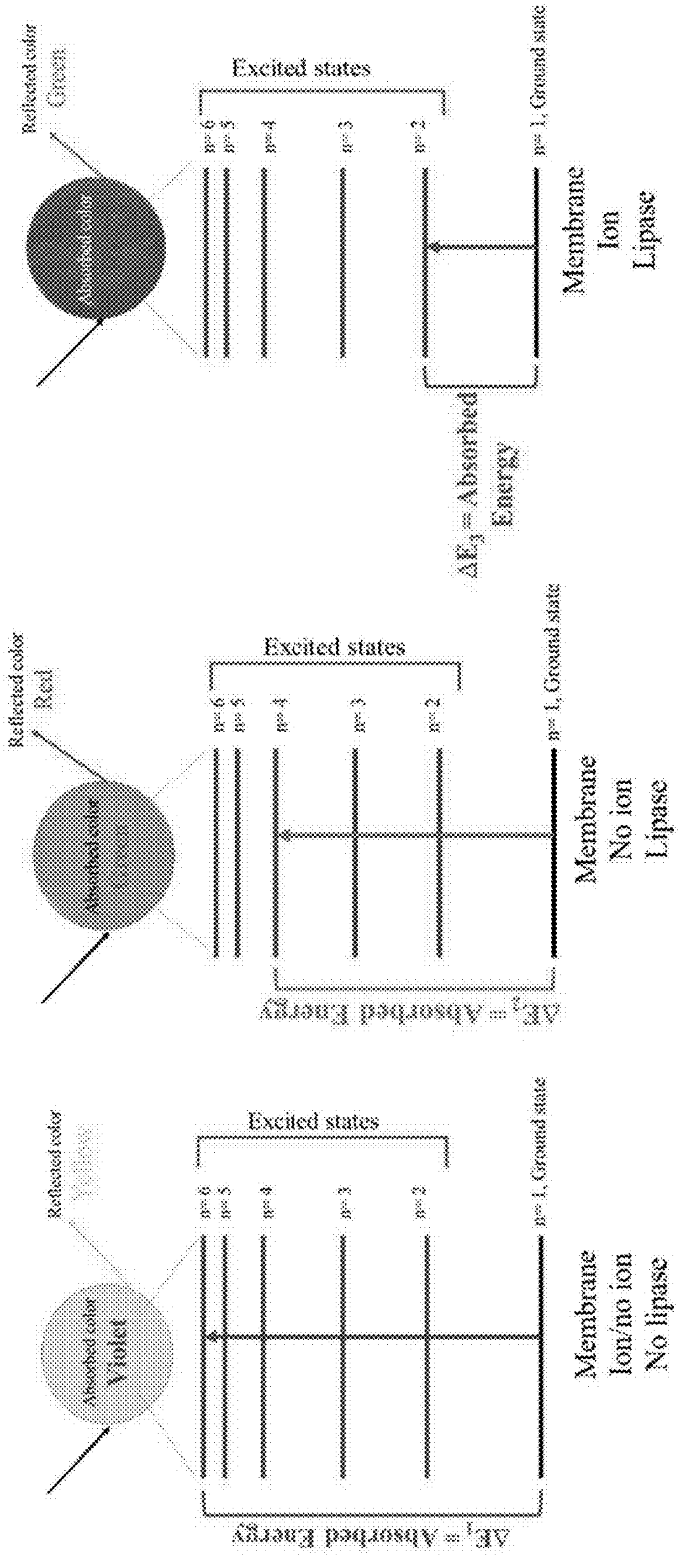
FIG. 22 Shows schematic of color-changing response of membrane: a) in absence of lipase b) in presence of lipase without ions and c) in the presence of lipase and ion.

After confirming that the green extraction consists of red and yellow forms of HCy, an additional experiment was conducted to analyze the phenomenon of green rather than red color changing. Dissolved HCy and membranes were exposed to lipase under various conditions to evaluate color changing response of the membranes and find the contributors of green color changing (FIG. 20). CS-PU membranes without PVP were submersed in either DI water or PBS (an ion containing environment). The CS-PU membrane did not show any color changing response in water or PBS solution without lipase. However, in the presence of lipase, membranes showed different color changing in water vs. PBS solution. In the absence of ions, the membranes showed red color changing while the presence of ions caused green color changing. On the other hand, dye solutions (without incorporation into membrane) showed red color changing even in the presence of ions. Hence, it can be concluded that green color changing requires three contributors: lipase (for cleavage), membrane polymers and ions. Differences between red and green color changing were not due to differences in the chemical structure of cleaved HCy based on MS and ATR-FTIR characterization. Additionally, the extraction from green membranes showed red color after drying. Therefore, the phenomenon resulting in the green observed color can be attributed to the band gap of electrons in the cleaved dye. When there are no ions in environment, more energy is needed to excite electrons. Therefore, visible light with higher energy and shorter wavelength (cyan light) is absorbed by membrane and red color is reflected. The same mechanism occurs in the absence of polymers in the dye solution. However, when both ions and membrane polymers are present, they have a synergic effect and decrease the band gap of electrons which results in lower energy needed for excitation of electrons. Therefore, magenta light is absorbed and green is reflected (FIG. 22). Overall, we have confirmed that the color changing to green or red are both attributed to the cleavage of HCy, and we can exclude factors other than dye cleavage as the major reason for the observed color change.

Materials and Methods Materials

Hexanoic acid (≥99%), 1-ethyl-3-(3-(dimethylamino)propyl)carbodiimide hydrochloride (EDC, 98%), 4-(dimethylamino)-pyridine (DMAP, 99%), dichloromethane (DCM, ≥99.5%), ethyl acetate (EtOAc, ≥99.5%), hexane (≥98.5%), methanol (≥99.8%), N,N-dimethylformamide (DMF, ≥99.8%), tetrahydrofuran (THF, ≥99.9%), polyvinylpyrrolidone (PVP, Mw 40,000) and polyethylene glycol (PEG, Mw 35,000) were purchased from Sigma Aldrich (St. Louis, MO, USA). Integra Miltex Standard biopsy punches, LB agar (Lennox) and LB broth (Lennox) were purchased from Fisher Scientific (Nepean, ON, Canada). Tecophilic HP-60D-35 (hydrophilic aliphatic polyurethane, PU) was purchased from Lubrizol Advanced Materials (Cleveland, OH, USA). The Lipase Activity Assay Kit (Colorimetric-ab 10254) was purchased from Abcam Inc (Toronto, ON, Canada). Clinical isolates of healthcare-associated MRSA (HA-MRSA) isolate #70065, community-associated MRSA (HA-MRSA) isolate #70527, and multi-drug-resistant *P. aeruginosa* isolate #73104 were obtained from the CANWARD (Canadian Ward Surveillance) study assessing antimicrobial resistance in Canadian hospitals, www.canr.ca. MRSA ATCC 33592 and *P. aeruginosa* ATCC 27853 were obtained from the American Type Culture Collection (ATCC) (Manassas, VA). *P. aeruginosa* PA01 was kindly provided by Dr. Ayush Kumar at the University of Manitoba.

Synthesis of HCy

Compound 1 (Scheme 1) was synthesized by condensation of 4-hydroxybenzaldehyde with 2-dicyanomethylene-3-cyano-4,5,5-trimethyl-2,5-dihydrofuran according to the reported procedures (17). Subsequently, a mixture of hexanoic acid 2 (0.064 g, 0.41 mmol), EDC (0.078 g, 0.41 mmol) and DMAP (0.05 g, 0.41 mmol) in 15 ml dry DCM was stirred under nitrogen at room temperature for 20 minutes. Compound 1 (0.10 g, 0.33 mmol) was then added and stirring was continuing overnight at room temperature. Upon completion of reaction, DCM was evaporated to get the crude product which was purified by column chromatography using 15-20% EtOAc/hexane followed by recrystallization from methanol to yield pure HCy in 80% yield. 1H NMR (CDCl3, 300 MHz) δ 7.65-7.72 (m, 3H), 7.27 (d, J=8.6 Hz, 2H), 7.02 (d, J=16.5 Hz, 1H), 2.62 (t, J=7.6 Hz, 2H), 1.84 (s, 8H), 1.41-1.46 (m, 4H), 0.97 (t, J=7.05 Hz, 3H). 13C NMR (DMSO-d6, 75 MHz): δ 177.5, 175.5, 172.0, 153.8, 146.7, 132.4, 131.3, 123.2, 115.8, 113.1, 112.3, 111.2, 100.1, 55.0, 33.9, 31.0, 25.5, 24.4, 22.3, 14.3. MS (ESI): m/z calcd for C24H23N3O3: 401.1739. Found: 400.1651 [M-1]+. FTIR max (cm-1): 2980-2781 (C—H stretch), 2222 (C N stretch), 1770 (C═O stretch), 1255 (C—O stretch).

Scheme 1. Synthetic scheme for the synthesis of HCy.

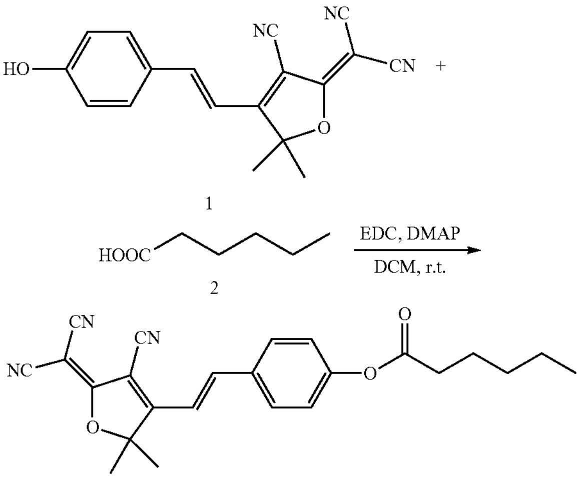

1

2

HCy

Fabrication of Electrospun Membranes

HCy-loaded electrospun membranes were prepared by conventional or coaxial electrospinning according to the parameters listed in Table 5. The primary membranes included a core-shell PU nanofibrous membrane (CS-PU) and a conventional (single) PU nanofibrous membrane (S-PU) to study the effects of enriching the surface of the nanofibers with HCy. Furthermore, two additional membranes were fabricated incorporating water soluble polymers PVP or PEG into the shell to investigate the suitability of blended water insoluble and soluble polymers to enhance sensitivity, either through the hypothesized mechanism of pore formation, increased swellability and hydrophilicity, stabilization of the cleaved state of the dye or enhanced color change via charge transfer interactions. Shell polymer ratios were 4:1 PU:PVP, 2:1 PU:PVP and 2:1 PU:PEG. In preparation for electrospinning, polymers were dissolved in 1:1 DMF:THF and stirred for 18-24 h at 45° C. prior to electrospinning to ensure homogeneity.

TABLE 5

Composition and electrospinning parameters of electrospun membranes

| | Shell | | | | | Electrospinning Parameters | | | |
|---|---|---|---|---|---|---|---|---|---|
| Sample | PU (w/v %) | PVP (w/v %) | HC (mass ratio)[1] | HC (w/v %) | Core PU (w/v %) | Shell rate (mL/h) | Core rate (mL/h) | dist (cm) | V (kV) |
| S-PU | 7.0 | — | 10:1 | 0.7 | — | 2.8 | — | 18.0 | 24.6 |
| CS-PU | 7.0 | — | 10:1 | 0.7 | 6.0 | 1.4 | 0.8 | 15.0 | 17.0 |
| CS-PU:PVP 4:1 | 7.0 | 1.75 | 10:1 | 0.875 | 6.0 | 1.4 | 0.8 | 15.0 | 17.0 |
| CS-PU:PVP 2:1 | 7.0 | 3.5 | 10:1 | 1.05 | 6.0 | 1.4 | 0.8 | 15.0 | 17.0 |
| CS-PU:PEG 2:1 | 7.0 | 3.5 | 10:1 | 1.05 | 6.0 | 0.9 | 0.5 | 15.0 | 17.0 |

[1]HC mass ratio represents ratio of shell polymer mass to the mass.

Nanofibers were electrospun onto an aluminum foil covered collector using an NE300 electrospinner (Inovenso, Turkey) according to the parameters shown in Table 5. Voltage and needle-collector distance were maintained at a constant value, 17.0 kV and 15.0 cm respectively, to ensure consistent conditions between the core-shell electrospun membranes. For the conventional single PU nanofibrous membrane, parameters were selected based on optimal jet formation. Membranes were vacuum dried for 24 h after electrospinning to remove residual solvent.

Nanofiber Morphology

Morphology of the electrospun nanofibers was characterized using scanning electron microscopy (SEM, FEI Quanta FEG 650). Samples were sputter coated for 45 seconds with gold-palladium (60:40) and SEM was conducted with an accelerating voltage of 10.0 kV. Fiber diameters were measured from SEM images using ImageJ. Core-shell morphology was confirmed by transmission electron microscopy (TEM, FEI Talos F200X). 0.3 mg/mL ZnO was incorporated into the core solution for electrospinning nanofibers for TEM to improve contrast for imaging. Nanofibers were deposited directly onto a copper-coated TEM grid. The grid was secured directly to the collector and electrospinning was conducted for 10-15 seconds. Images were collected at an accelerating voltage of 200 kV.

Chemical Characterization of HCy and Electrospun Membranes

The chemical structure of the HCy was confirmed by transmission Fourier transform infrared (transmission FTIR, Thermo Scientific, Nicolet is 10), 1H-nuclear magnetic resonance (1H-NMR, Bruker, Karlsruhe, Germany, Avance 300), 13C-nuclear magnetic resonance (13C NMR, Bruker, Karlsruhe, Germany, Avance 300) and electrospray ionization mass spectrometry (ESI MS, Bruker Compact). Membranes pre- and post-electrospinning were analyzed with attenuated total reflectance-Fourier transform infrared (ATR-FTIR, Thermo Scientific, Nicolet is 10).

Bacteria Culture

Membranes were tested for in vitro chromogenic response toward two clinically relevant species of bacteria: MRSA (ATCC 33592, strain #70527 and strain #70065) and *P. aeruginosa* (ATCC 27853, PA01 and strain #73104). MRSA and *P. aeruginosa* species were selected for the development of a diagnostic wound dressing since they are among the most common causes of bacterial infection in both acute and chronic wounds.

MRSA or *P. aeruginosa* were streaked on LB agar and incubated for 18 h at 37° C. For the preparation of overnight broth culture, MRSA or *P. aeruginosa* colonies were suspended in 0.01 M PBS to a turbidity of 0.5 MF and diluted by a factor of 100× in 0.01 M PBS, followed by adding 15.0 L of the diluted suspension to 45.0 mL LB broth. The broth culture was incubated for 18 h at 37° C. with shaking at 140 rpm.

Colorimetric Response to Lipase

The color changing behavior of S-PU, CS-PU and CS-PU:PVP 2:1 was evaluated in response to commercial *P. cepacia* lipase as well as supernatants from cultured MRSA and *P. aeruginosa*. Commercial *P. cepacia* lipase was diluted with 0.01 M PBS to produce various concentrations in the range of 0.00125 mg/mL-0.5 mg/mL. Membrane samples (1.0 cm2) were immersed in the diluted lipase and monitored for color change for 8 h. Moreover, S-PU, CS-PU and CS-PU:PVP 2:1 were tested in response to bacterial supernatants of *P. aeruginosa* (ATCC 27853) and MRSA (ATCC 33592). Bacterial suspensions were diluted to concentrations of 107, 106, 105 and 104 CFU/mL. The suspensions were spun down for 15 minutes at 10,000 g (SORVALL LEGEND MICRO21, Thermo scientific) to remove the bacterial cells in order to evaluate the membranes only in the presence of enzyme secreted from a known concentration of bacteria, without bacteria growth throughout the duration of the test. The collected supernatants were used to evaluate color changing response of S-PU, CS-PU and CS-PU:PVP 2:1 after 24 h.

Colorimetric Response to Bacteria

To prepare bacterial lawns, overnight suspensions prepared as previously described were diluted by a factor of 100× and spread on LB agar (100 μL) followed by incubation at 37° C. for various time intervals (3 h, 4 h, 5 h, 8 h and 24 h) to produce bacterial lawns in a range of concentrations. After the incubation, 1 cm×1 cm membrane samples were placed directly onto the lawns and monitored by naked eye for a color change for 3 h at 37° C. The reflectance spectra of the membranes were measured by spectrophotometer (GretagMacbeth ColorEye® 2180UV) with CIE Illuminant C and 2° through the glass of the Petri dish, as reported by Yapor et al. 20. Color difference between samples and the controls were calculated according to the following equation:

$$\Delta E^2 = \sqrt{(L-L_o)^2+(\alpha-a_o)^2+(b+b_c)^2}$$

Where L, a and b are lightness, CIE coordinate of green and red, and CIE coordinate of blue and yellow, respectively. The subscript c refers to the control. Photos and spectrophotometer readings were taken at 0 h, 1 h, 2 h and 3 h. Bacterial concentration was quantified immediately after membranes were placed on the lawns at 0 h. To quantify the lawn concentration, cylindrical agar plugs were removed from the lawns with an Integra Miltex Standard Biopsy Punch and vortexed for 2 minutes in 1.0 mL PBS to detach the bacteria from the surface of the agar. The concentrations of the bacterial suspensions were quantified according to standard drop-plating procedure. Briefly, the suspensions were subjected to serial 10-fold dilutions in PBS followed by plating 30.0 μL drop by drop onto LB agar. Colonies were counted after incubation for 18 h at 37° C.

Ex Vivo Colorimetric Response

An ex vivo porcine model was implemented as previously described to assess the performance of the wound dressings in a model burn wound (16). Briefly, pigskin was cut to dimensions of 4.0 cm×4.0 cm. A brass rod (2.0 cm×2.0 cm with a weight of 9.2 N) was heated in boiling water for 10 minutes and placed in the center of pigskin for 1 minute without external force. The burnt skins were immersed in saline (0.9% NaCl) for 10 minutes. The prepared pigskins were sterilized with 70% EtOH and air dried before further use (16). Samples were inoculated with three strains of *P. aeruginosa* (PA01, 73104 and 27853) and MRSA (70527, 33592 and 70065). Bacterial suspensions were prepared as previously mentioned. Briefly, 20 μL of bacterial suspension was spread on the wound site and incubated for 5 h before placing the membranes (1.0 cm×1.0 cm) directly on the wound site. The color changing response of the membrane was monitored by the naked eye, with photos taken after 2 h and 24 h at 37° C. The reflectance spectra of the membranes after 24 h incubation were measured by spectrophotometer (GretagMacbeth ColorEye® 2180UV) with CIE Illuminant C and 2° observer. Membranes were sandwiched between two slides and placed directly into the sample port of the spectrophotometer. The initial bacteria concentration in CFU/cm$^2$ was calculated as herein. Furthermore, a multi-species ex vivo model was implemented to evaluate the colorimetric response of membranes in a realistic situation. For this experiment, 20 μL of 1:1 *P. aeruginosa* (ATCC 27853) and MRSA (ATCC 33592) suspensions with initial concentration 108 CFU/mL were spread on the pigskin and incubated for 5 h (37° C.). The pigskins were monitored for 24 h to investigate the color changing of membranes (S-PU, CS-PU and CS-PU:PVP 2:1) with photos taken at 1 h and 24 h. Since the color changing response of the membranes is dependent on lipase activity, we quantified the relationship between lipase activity and bacterial concentration in the ex vivo porcine wound model. Various concentrations of *P. aeruginosa* (ATCC 27853) and MRSA (ATCC 33592) were spread on the wounded pigskin and incubated for 5 h. A 4.0 mm biopsy punch was used to remove a sample of skin tissue which was suspended in 1 mL assay buffer and sonicated for 2 minutes, followed by 20 seconds vortexing. The prepared suspensions were spun down for 15 minutes at 10,000 g before transferring 50 μL of each solution to a 96-well plate. The lipase assay was conducted according to the manufacturer's protocol using a microplate reader (BioTek-PowerWave XS2) in kinetic mode, at 37° C. with readings every 2 min for 1 h.

Characterization of Lipase-Cleaved Dyes

The structure of HCy post-exposure to bacteria was analyzed by ESI MS and ATR-FTIR to confirm its cleavage. Dyes were extracted from the electrospun membranes post-exposure to bacteria by submersing the membranes in ethyl acetate for 24 h, followed by filtration with 0.2 μm syringe filter.

HCy was also exposed to a commercial lipase and then characterized for comparison to the membranes exposed to bacteria. HCy hydrolysate was prepared by suspending 50 μM HCy in a solution of 10 μg/mL commercially available lipase from *P. cepacia* in PBS (0.01 M, pH 7.4) with 5% DMSO. The solution was incubated at 37° C. overnight to give sufficient time for cleavage of yellow HCy to produce the red phenol form. The pH of the orange dye solution was adjusted to pH 8.23 and the yellow dye was separated from the red cleaved dye by precipitation. The dye solution was centrifuged at 14 800 rpm to remove unhydrolyzed yellow HCy, and the red product was extracted from the aqueous phase with ethyl acetate and dried to obtain a red powder. The purified lipase-cleaved red dye was analyzed by ESI MS for comparison to dyes extracted from green membranes post-exposure to bacteria.

Statistical Analysis

Data are presented as mean±standard deviation (SD). The number of replicates is indicated as the n-value. One-way analysis of variance was performed on all results with $p<0.05$ considered to be significant.

While the preferred embodiments of the invention have been described above, it will be recognized and understood that various modifications may be made therein, and the appended claims are intended to cover all such modifications which may fall within the spirit and scope of the invention.

In the preceding description, for purposes of explanation, numerous details are set forth in order to provide a thorough understanding of the embodiments. However, it will be apparent to one skilled in the art that these specific details are not required. For example, specific details are not provided as to whether the embodiments described herein are implemented using computer hardware or software, or a combination thereof.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

The following references are hereby incorporated by reference.

Augustine et al., Electrospun PCL membranes incorporated with biosynthesized silver nanoparticles as antibacterial wound dressings, Appl. Nanosci. 6 (2016) 337-344. doi: 10.1007/s13204-015-0439-1.

Bean et al., Triggered release of Bacteriophage K from agarose/hyaluronan hydrogel matrixes by *Staphylococcus aureus* virulence factors, Chem. Mater. 26 (2014) 7201-7208. doi:10.1021/cm503974 g.

Craig et al., Bacterial protease triggered release of biocides from microspheres with an oily core, Colloids Surfaces B Biointerfaces. 127 (2015) 200-205. doi:10.1016/j.colsurfb.2015.01.036.
He et al., Fabrication of metronidazole loaded poly (ε-caprolactone)/zein core/shell nanofiber membranes via coaxial electrospinning for guided tissue regeneration, J. Colloid Interface Sci. 490 (2017) 270-278. doi:10.1016/j.jcis.2016.11.062.
Hoang et al., Degradation of polyethylene succinate (PES) by a new thermophilic Microbispora strain, Biodegradation. 18 (2007) 333-342. doi:10.1007/s10532-006-9067-5.
Thet et al., Prototype Development of the Intelligent Hydrogel Wound Dressing and Its Efficacy in the Detection of Model Pathogenic Wound Biofilms, ACS Appl. Mater. Interfaces. 8 (2016) 14909-14919. doi:10.1021/acsami.5b07372.
Traba & Liang, Bacteria responsive antibacterial surfaces for indwelling device infections, J. Control. Release. 198 (2015) 18-25. doi:10.1016/j.jconrel.2014.11.025.
Xiong et al., Lipase-sensitive polymeric triple-layered nanogel for "on-demand" drug delivery, J. Am. Chem. Soc. 134 (2012a) 4355-4362. doi:10.1021/ja211279u.
Xiong et al., Bacteria-Responsive Multifunctional Nanogel for Targeted Antibiotic Delivery, Advanced Materials, 24(46) December (2012) 6175-6180. doi: 10.1002/adma.201202847.
Yang et al., Promotion of skin regeneration in diabetic rats by electrospun core-sheath fibers loaded with basic fibroblast growth factor, Biomaterials. 32 (2011) 4243-4254. doi:10.1016/j.biomaterials.2011.02.042.
Cefalu, J. E.; Barrier, K. M.; Davis, A. H. Wound Infections in Critical Care. Crit. Care Nurs. Clin. North Am. 2017, 29, 81-96.
Edwards, R.; Harding, K. G. Bacteria and Wound Healing. Curr. Opin. Infect. Dis. 2004, 17, 91-96.
Tsiouris, C. G.; Tsiouri, M. G. Human Microflora, Probiotics and Wound Healing. Wound Med. 2017, 19, 33-38.
Gardner, S. E.; Frantz, R. A.; Doebbeling, B. N. The Validity of the Clinical Signs and Symptoms Used to Identify Localized Chronic Wound Infection. Wound Repair Regen. 2001, 9 (3), 178-186.
Martin, J. M.; Zenilman, J. M.; Lazarus, G. S. Molecular Microbiology: New Dimensions for Cutaneous Biology and Wound Healing. J. Invest. Dermatol. 2010, 130, 38-48.
Dow, G. Bacterial Swabs and the Chronic Wound: When, How, and What Do They Mean? Ostomy Wound Manag. 2003, 49-5A Supp (5A Suppl), 8-13.
European Wound Management Association (EWMA). Position Document: Identifying Criteria for Wound Infection; London: MEP Ltd, 2006.
Li, S.; Renick, P. J.; Senkowsky, J.; Nair, A. M.; Tang, L. Diagnostics for Wound Infections. Adv. Wound Care 2020, 1-36. https://doi.org/10.1089/wound.2019.1103.
Zhou, J.; Yao, D.; Qian, Z.; Hou, S.; Li, L.; Jenkins, A. T. A.; Fan, Y. Bacteria-Responsive Intelligent Wound Dressing: Simultaneous In Situ Detection and Inhibition of Bacterial Infection for Accelerated Wound Healing. Biomaterials 2018, 161, 11-23.
Sun, Y.; Zhao, C.; Niu, J.; Ren, J.; Qu, X. Colorimetric Band-Aids for Point-of-Care Sensing and Treating Bacterial Infection. ACS Cent. Sci. 2020, 6 (2), 207-212. (11) Thet, N. T.; Alves, D. R.; Bean, J. E.; Booth, S.; Nzakizwanayo, J.; Young, A. E. R.; Jones, B. V.; Jenkins, A. T. A. Prototype Development of the Intelligent Hydrogel Wound Dressing and Its Efficacy in the Detection of Model Pathogenic
Wound Biofilms. ACS Appl. Mater. Interfaces 2016, 8 (24), 14909-14919.
(Liu, L.; Li, X.; Nagao, M.; Elias, A. L.; Narain, R.; Chung, H. J. A PH-Indicating Colorimetric Tough Hydrogel Patch towards Applications in a Substrate for Smart Wound Dressings. Polymers (Basel). 2017, 9 (558), 1-15.
Liu, S. J.; Kau, Y. C.; Chou, C. Y.; Chen, J. K.; Wu, R. C.; Yeh, W. L. Electrospun PLGA/Collagen Nanofibrous Membrane as Early-Stage Wound Dressing. J. Memb. Sci. 2010, 355, 53-59.
Lin, H. T.; Venault, A.; Chang, Y. Zwitterionized Chitosan Based Soft Membranes for Diabetic Wound Healing. J. Memb. Sci. 2019, 591, 117319.
Venault, A.; Lin, K. H.; Tang, S. H.; Dizon, G. V.; Hsu, C. H.; Maggay, I. V. B.; Chang, Y. Zwitterionic Electrospun PVDF Fibrous Membranes with a Well-Controlled Hydration for Diabetic Wound Recovery. J. Memb. Sci. 2020, 598, 117648.
Singh, H.; Li, W.; Kazemian, M. R.; Yang, R.; Yang, C.; Logsetty, S.; Liu, S. Lipase-Responsive Electrospun Theranostic Wound Dressing for Simultaneous Recognition and Treatment of Wound Infection. ACS Appl. Bio Mater. 2019, 2 (5), 2028-2036.
Teng, X.; Tian, M.; Zhang, J.; Tang, L.; Xin, J. A TCF-Based Colorimetric and Fluorescent Probe for Palladium Detection in an Aqueous Solution. Tetrahedron Lett. 2018, 59 (29), 2804-2808.
Bowler, P. G.; Duerden, B. I.; Armstrong, D. G. Wound Microbiology and Associated Approaches to Wound Management. Clin. Microbiol. Rev. 2001, 14 (2), 244-269.
Bessa, L. J.; Fazii, P.; Di Giulio, M.; Cellini, L. Bacterial Isolates from Infected Wounds and Their Antibiotic Susceptibility Pattern: Some Remarks about Wound Infection. Int. Wound J. 2015, 12 (1), 47-52.
Yapor, J. P.; Alharby, A.; Gentry-Weeks, C.; Reynolds, M. M.; Alam, A. K. M. M.; Li, Y. V. Polydiacetylene Nanofiber Composites as a Colorimetric Sensor Responding to *Escherichia coli* and PH. ACS Omega 2017, 2 (10), 7334-7342.
Ross, J. A.; Allan, N.; Olson, M.; Schatz, C.; Nation, P. N.; Gawaziuk, J. P.; Sethi, J.; Liu, S.; Logsetty, S. Comparison of the Efficacy of Silver-Based Antimicrobial Burn Dressings in a Porcine Model of Burn Wounds. Burns 2020. https://doi.org/10.1016/j.burns.2020.04.004.
Majewski, W.; Cybulski, Z.; Napierala, M.; Pukacki, F.; Staniskewski, R.; Pietkiewicz, K.; Zapalski, S. The Value of Quantitative Bacteriological Investigations in the Monitoring of Treatment of Ischaemic Ulcerations of Lower Legs. Int. Angiol. 1995, 14, 381-384.
Raahave, D.; Friis-Møller, A.; Bjerre-Jepsen, K.; Thiis-Knudsen, J.; Rasmussen, L. The Infective Dose of Aerobic and Anaerobic Bacteria in Postoperative Wound Sepsis. Arch. Surg. 1986, 121, 924-929.
De Queiroz, A. A. A.; Soares, D. A. W.; Trzesniak, P.; Abraham, G. A. Resistive-Type Humidity Sensors Based on PVP-Co and PVP-I2 Complexes. J. Polym. Sci. Part B Polym. Phys. 2001, 39, 459-469.
Borodko, Y.; Humphrey, S. M.; Tilley, T. D.; Frei, H.; Somorjai, G. A. Charge-Transfer Interaction of Poly(Vinylpyrrolidone) with Platinum and Rhodium Nanoparticles. J. Phys. Chem. C 2007, 111 (17), 6288-6295.
Dessouki, A. M.; Taher, N. H.; El-Arnaouty, M. B. Gamma Ray Induced Graft Copolymerization of N-Vinylpyrrolidone, Acrylamide and Their Mixtures onto Polypropylene Films. Polym. Int. 1998, 45 (1), 67-76.

Ruostesuo, P.; Peltola, K.; Salminen, U.; Hakkinen, A. M. Charge Transfer Complexes of N-Substituted 2-Pyrrolidinones. Spectrochim. Acta 1988, 44A (1), 63-67.

Spindler, R.; Shriver, D. F. Physical and Spectroscopic Properties of Ternary Polymer Electrolytes Composed of Poly(Vinylpyrrolidone), Poly(Ethylene Glycol), and Lithium Trifluoromethanesulfonate. Macromolecules 1986, 19 (2), 347-350.

Boardman, C.; Jarvis, A. N. The Prevention of In-Wash Dye Transfer. Rev. Prog. Color. Relat. Top. 2000, 30 (1), 63-66.

Voronova, M.; Rubleva, N.; Kochkina, N.; Afineevskii, A.; Zakharov, A.; Surov, O. Preparation and Characterization of Polyvinylpyrrolidone/Cellulose Nanocrystals Composites. Nanomaterials 2018, 8 (12), 1-21.

Yu, Z. J.; Kumar, M. R.; Sun, D. L.; Wang, L. T.; Hong, R. Y. Large Scale Production of Hexagonal ZnO Nanoparticles Using PVP as a Surfactant. Mater. Lett. 2016, 166, 284-287.

Cai, C.; Qiu, X.; Zeng, M.; Lin, M.; Lin, X.; Lou, H.; Zhan, X.; Pang, Y.; Huang, J.; Xie, L. Using Polyvinylpyrrolidone to Enhance the Enzymatic Hydrolysis of Lignocelluloses by Reducing the Cellulase Non-Productive Adsorption on Lignin. Bioresour. Technol. 2017, 227, 74-81.

Pallapolu, V. R.; Shi, S.; Kang, L.; Kothari, U.; Li, J. Boost Effect of Water-Soluble Polymers on Enzymatic Hydrolysis of Lignocellulosic Biomass. Ind. Eng. Chem. Res. 2020, 59, 5186-5193.

What is claimed is:

1. A bacteria-responsive nanofiber, comprising:

a core-shell nanofiber structure that comprises polyurethane (PU) and a polyvinylpyrrolidone (PVP) dopant in the shell, and a hemicyanine dye localized in the core-shell nanofiber at the surface of the shell, wherein said hemicyanine dye is bound to hexanoic acid and comprises a labile ester linkage that is enzymatically cleavable by bacterial lipase, and wherein said hemicyanine dye in said shell exhibits a color-change response to bacterial lipase and said color change is visible to the naked eye.

2. The core-shell nanofiber of claim 1, wherein said labile ester linkage is enzymatically cleavable by bacterial lipase released from at least one of *Pseudomonas aeruginosa* and methicillin-resistant *Staphylococcus aureus* (MRSA).

3. The core-shell nanofiber of claim 2, wherein said labile ester linkage is enzymatically cleavable by *Pseudomonas aeruginosa* and methicillin-resistant *Staphylococcus aureus* (MRSA) at concentrations above $2.5\times10^5$ CFU/$cm^2$ and $1.0\times10^6$ CFU/$cm^2$, respectively.

4. A bacteria-responsive color-changing nanofibrous nanofiberous membrane, said membrane comprising a plurality of core-shell nanofibers, wherein said core-shell nanofibers comprise polyurethane (PU) and a polyvinylpyrrolidone (PVP) dopant in the shell in the range of PU:PVP 4:1 to PU:PVP 2:1, and a hemicyanine dye localized in the core-shell nanofiber at the surface of the shell, wherein said hemicyanine dye is bound to hexanoic acid, and wherein said hemicyanine dye in said shell exhibits a color-change response to bacterial lipase and said color change is visible to the naked eye.

5. The bacteria-responsive color-changing nanofibrous membrane of claim 4, wherein said hemicyanine dye comprises a labile ester linkage that is enzymatically cleavable by bacterial lipase released from at least one of *Pseudomonas aeruginosa* and methicillin-resistant *Staphylococcus aureus* (MRSA).

6. The bacteria-responsive color-changing nanofibrous membrane of claim 5, wherein said labile ester linkage is enzymatically cleavable by *Pseudomonas aeruginosa* and methicillin-resistant *Staphylococcus aureus* (MRSA) at concentrations above $2.5\times10^5$ CFU/$cm^2$ and $1.0\times10^6$ CFU/$cm^2$, respectively.

7. The bacteria-responsive color-changing nanofibrous membrane of claim 4, wherein said core-shell nanofibers are electrospun to form said membrane.

* * * * *